(12) United States Patent
Jin et al.

(10) Patent No.: US 7,811,231 B2
(45) Date of Patent: Oct. 12, 2010

(54) CONTINUOUS GLUCOSE MONITORING SYSTEM AND METHODS OF USE

(75) Inventors: Robert Y Jin, Lafayette, CA (US); Mark K. Sloan, Hayward, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 117 days.

(21) Appl. No.: 10/745,878

(22) Filed: Dec. 26, 2003

(65) Prior Publication Data

US 2004/0186365 A1 Sep. 23, 2004

Related U.S. Application Data

(60) Provisional application No. 60/437,374, filed on Dec. 31, 2002.

(51) Int. Cl.
*A61B 5/00* (2006.01)
*G08B 1/08* (2006.01)
*G06F 7/00* (2006.01)
*G06F 17/00* (2006.01)

(52) U.S. Cl. .................. 600/300; 600/365; 340/539.12; 707/621

(58) Field of Classification Search ......... 600/300–301, 600/481, 483, 500–503, 508–509, 513, 523, 600/529, 532, 538, 544–545; 128/903–905, 128/920–925; 705/2–4; 340/539, 573
See application file for complete search history.

(56) References Cited

U.S. PATENT DOCUMENTS 3,260,656 A 7/1966 Ross, Jr.
3,304,413 A 2/1967 Lehmann et al.
3,651,318 A 3/1972 Czekajewski (Continued)

FOREIGN PATENT DOCUMENTS

DE 2903216 8/1979

(Continued)

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

(Continued)

*Primary Examiner*—Henry M Johnson, III
*Assistant Examiner*—Shirley Jian
(74) *Attorney, Agent, or Firm*—Jackson & Co., LLP

(57) ABSTRACT

A continuous glucose monitoring system including a sensor configured to detect one or more glucose levels, a transmitter operatively coupled to the sensor, the transmitter configured to receive the detected one or more glucose levels, the transmitter further configured to transmit signals corresponding to the detected one or more glucose levels, and a receiver operatively coupled to the transmitter configured to receive transmitted signals corresponding to the detected one or more glucose levels, and methods thereof, are disclosed. In one aspect, the transmitter may be configured to transmit a current data point and at least one previous data point, the current data point and the at least one previous data point corresponding to the detected one or more glucose levels.

49 Claims, 6 Drawing Sheets

U.S. PATENT DOCUMENTS

| | | | |
|---|---|---|---|
| 3,653,841 A | 4/1972 | Klein | |
| 3,698,386 A | 10/1972 | Fried | |
| 3,719,564 A | 3/1973 | Lilly, Jr. et al. | |
| 3,768,014 A | 10/1973 | Smith et al. | |
| 3,776,832 A | 12/1973 | Oswin et al. | |
| 3,837,339 A | 9/1974 | Aisenberg et al. | |
| 3,919,051 A | 11/1975 | Koch et al. | |
| 3,926,760 A | 12/1975 | Allen et al. | |
| 3,972,320 A | 8/1976 | Kalman | |
| 3,979,274 A | 9/1976 | Newman | |
| 4,008,717 A | 2/1977 | Kowarski | |
| 4,016,866 A | 4/1977 | Lawton | |
| 4,036,749 A | 7/1977 | Anderson | |
| 4,055,175 A | 10/1977 | Clemens et al. | |
| 4,059,406 A | 11/1977 | Fleet | |
| 4,076,596 A | 2/1978 | Connery et al. | |
| 4,098,574 A | 7/1978 | Dappen | |
| 4,100,048 A | 7/1978 | Pompei et al. | |
| 4,129,128 A | 12/1978 | McFarlane | |
| 4,151,845 A | 5/1979 | Clemens | |
| 4,154,231 A | 5/1979 | Russell | |
| 4,168,205 A | 9/1979 | Danninger et al. | |
| 4,172,770 A | 10/1979 | Semersky et al. | |
| 4,178,916 A | 12/1979 | McNamara | |
| 4,206,755 A | 6/1980 | Klein | |
| 4,224,125 A | 9/1980 | Nakamura et al. | |
| 4,240,438 A | 12/1980 | Updike et al. | |
| 4,240,889 A | 12/1980 | Yoda et al. | |
| 4,245,634 A | 1/1981 | Albisser et al. | |
| 4,247,297 A | 1/1981 | Berti et al. | |
| 4,271,449 A | 6/1981 | Grogan | |
| 4,318,784 A | 3/1982 | Higgins et al. | |
| 4,327,725 A | 5/1982 | Cortese et al. | |
| 4,331,869 A | 5/1982 | Rollo | |
| 4,340,458 A | 7/1982 | Lerner et al. | |
| 4,344,438 A | 8/1982 | Schultz | |
| 4,352,960 A | 10/1982 | Dormer et al. | |
| 4,356,074 A | 10/1982 | Johnson | |
| 4,365,637 A | 12/1982 | Johnson | |
| 4,366,033 A | 12/1982 | Richter et al. | |
| 4,375,399 A | 3/1983 | Havas et al. | |
| 4,384,586 A | 5/1983 | Christiansen | |
| 4,390,621 A | 6/1983 | Bauer | |
| 4,392,933 A | 7/1983 | Nakamura et al. | |
| 4,401,122 A | 8/1983 | Clark, Jr. | |
| 4,404,066 A | 9/1983 | Johnson | |
| 4,407,959 A | 10/1983 | Tsuji et al. | |
| 4,417,588 A | 11/1983 | Houghton et al. | |
| 4,418,148 A | 11/1983 | Oberhardt | |
| 4,420,564 A | 12/1983 | Tsuji et al. | |
| 4,425,920 A | 1/1984 | Bourland et al. | |
| 4,427,004 A | 1/1984 | Miller et al. | |
| 4,427,770 A | 1/1984 | Chen et al. | |
| 4,431,004 A | 2/1984 | Bessman et al. | |
| 4,436,094 A | 3/1984 | Cerami | |
| 4,440,175 A | 4/1984 | Wilkins | |
| 4,444,892 A | 4/1984 | Malmros | |
| 4,450,842 A | 5/1984 | Zick et al. | |
| 4,458,686 A | 7/1984 | Clark, Jr. | |
| 4,461,691 A | 7/1984 | Frank | |
| 4,467,811 A | 8/1984 | Clark, Jr. | |
| 4,469,110 A | 9/1984 | Slama | |
| 4,477,314 A | 10/1984 | Richter et al. | |
| 4,478,976 A | 10/1984 | Goertz et al. | |
| 4,483,924 A | 11/1984 | Tsuji et al. | |
| 4,484,987 A | 11/1984 | Gough | |
| 4,494,950 A | 1/1985 | Fischell | |
| 4,512,348 A | 4/1985 | Uchigaki et al. | |
| RE31,916 E | 6/1985 | Oswin et al. | |
| 4,522,690 A | 6/1985 | Venkatsetty | |
| 4,524,114 A | 6/1985 | Samuels et al. | |
| 4,526,661 A | 7/1985 | Steckhan et al. | |
| 4,527,240 A | 7/1985 | Kvitash | |
| 4,534,356 A | 8/1985 | Papadakis | |
| 4,538,616 A | 9/1985 | Rogoff | |
| 4,543,955 A | 10/1985 | Schroeppel | |
| 4,545,382 A | 10/1985 | Higgins et al. | |
| 4,552,840 A | 11/1985 | Riffer | |
| 4,560,534 A | 12/1985 | Kung et al. | |
| 4,569,589 A | 2/1986 | Neufeld | |
| 4,571,292 A | 2/1986 | Liu et al. | |
| 4,573,994 A | 3/1986 | Fischell et al. | |
| 4,581,336 A | 4/1986 | Malloy et al. | |
| 4,595,011 A | 6/1986 | Phillips | |
| 4,595,479 A | 6/1986 | Kimura et al. | |
| 4,619,754 A | 10/1986 | Niki et al. | |
| 4,619,793 A | 10/1986 | Lee | |
| 4,627,445 A | 12/1986 | Garcia et al. | |
| 4,627,908 A | 12/1986 | Miller | |
| 4,633,878 A | 1/1987 | Bombardieri | |
| 4,633,881 A | 1/1987 | Moore et al. | |
| 4,637,403 A | 1/1987 | Garcia et al. | |
| RE32,361 E | 2/1987 | Duggan | |
| 4,648,408 A | 3/1987 | Hutcheson et al. | |
| 4,650,547 A | 3/1987 | Gough | |
| 4,653,513 A | 3/1987 | Dombrowski | |
| 4,654,197 A | 3/1987 | Lilja et al. | |
| 4,655,880 A | 4/1987 | Liu | |
| 4,655,885 A | 4/1987 | Hill et al. | |
| 4,658,463 A | 4/1987 | Sugita et al. | |
| 4,671,288 A | 6/1987 | Gough | |
| 4,674,652 A | 6/1987 | Aten et al. | |
| 4,679,562 A | 7/1987 | Luksha | |
| 4,680,268 A | 7/1987 | Clark, Jr. | |
| 4,682,602 A | 7/1987 | Prohaska | |
| 4,684,537 A | 8/1987 | Graetzel et al. | |
| 4,685,463 A | 8/1987 | Williams | |
| 4,686,624 A | 8/1987 | Blum et al. | |
| 4,703,756 A | 11/1987 | Gough et al. | |
| 4,711,245 A | 12/1987 | Higgins et al. | |
| 4,717,673 A | 1/1988 | Wrighton et al. | |
| 4,721,601 A | 1/1988 | Wrighton et al. | |
| 4,721,677 A | 1/1988 | Clark, Jr. | |
| 4,726,378 A | 2/1988 | Kaplan | |
| 4,726,716 A | 2/1988 | McGuire | |
| 4,731,726 A | 3/1988 | Allen, III | |
| 4,749,985 A | 6/1988 | Corsberg | |
| 4,750,496 A | 6/1988 | Reinhart | |
| 4,757,022 A | 7/1988 | Shults et al. | |
| 4,758,323 A | 7/1988 | Davis et al. | |
| 4,759,371 A | 7/1988 | Franetzki | |
| 4,759,828 A | 7/1988 | Young et al. | |
| 4,764,416 A | 8/1988 | Ueyama et al. | |
| 4,776,944 A | 10/1988 | Janata et al. | |
| 4,777,953 A | 10/1988 | Ash et al. | |
| 4,779,618 A | 10/1988 | Mund et al. | |
| 4,781,798 A | 11/1988 | Gough | |
| 4,784,736 A | 11/1988 | Lonsdale et al. | |
| 4,795,707 A | 1/1989 | Niiyama et al. | |
| 4,796,634 A | 1/1989 | Huntsman et al. | |
| 4,803,625 A | 2/1989 | Fu et al. | |
| 4,805,624 A | 2/1989 | Yao et al. | |
| 4,813,424 A | 3/1989 | Wilkins | |
| 4,815,469 A | 3/1989 | Cohen et al. | |
| 4,820,399 A | 4/1989 | Senda et al. | |
| 4,822,337 A | 4/1989 | Newhouse et al. | |
| 4,830,959 A | 5/1989 | McNeil et al. | |
| 4,832,797 A | 5/1989 | Vadgama et al. | |
| 4,835,372 A | 5/1989 | Gombrich et al. | |
| RE32,947 E | 6/1989 | Dormer et al. | |
| 4,837,049 A | 6/1989 | Byers et al. | |
| 4,840,893 A | 6/1989 | Hill et al. | |
| RE32,974 E | 7/1989 | Porat et al. | |
| 4,844,076 A | 7/1989 | Lesho et al. | |

| | | | | | |
|---|---|---|---|---|---|
| 4,845,035 A | 7/1989 | Fanta et al. | 5,082,550 A | 1/1992 | Rishpon et al. |
| 4,848,351 A | 7/1989 | Finch | 5,082,786 A | 1/1992 | Nakamoto |
| 4,854,322 A | 8/1989 | Ash et al. | 5,084,828 A | 1/1992 | Kaufman et al. |
| 4,856,340 A | 8/1989 | Garrison | 5,089,112 A | 2/1992 | Skotheim et al. |
| 4,857,713 A | 8/1989 | Brown | 5,094,951 A | 3/1992 | Rosenberg |
| 4,858,617 A | 8/1989 | Sanders | 5,095,904 A | 3/1992 | Seligman et al. |
| 4,870,561 A | 9/1989 | Love et al. | 5,096,560 A | 3/1992 | Takai et al. |
| 4,871,351 A | 10/1989 | Feingold | 5,096,836 A | 3/1992 | Macho et al. |
| 4,871,440 A | 10/1989 | Nagata et al. | 5,101,814 A | 4/1992 | Palti |
| 4,874,499 A | 10/1989 | Smith et al. | 5,106,365 A | 4/1992 | Hernandez |
| 4,874,500 A | 10/1989 | Madou et al. | 5,108,564 A | 4/1992 | Szuminsky et al. |
| 4,890,620 A | 1/1990 | Gough | 5,109,850 A | 5/1992 | Blanco et al. |
| 4,890,621 A | 1/1990 | Hakky | 5,111,539 A | 5/1992 | Hiruta et al. |
| 4,894,137 A | 1/1990 | Takizawa et al. | 5,111,818 A | 5/1992 | Suzuki et al. |
| 4,897,162 A | 1/1990 | Lewandowski et al. | 5,114,678 A | 5/1992 | Crawford et al. |
| 4,897,173 A | 1/1990 | Nankai et al. | 5,120,420 A | 6/1992 | Nankai et al. |
| 4,899,839 A | 2/1990 | Dessertine et al. | 5,120,421 A | 6/1992 | Glass et al. |
| 4,909,908 A | 3/1990 | Ross et al. | 5,126,034 A | 6/1992 | Carter et al. |
| 4,911,794 A | 3/1990 | Parce et al. | 5,126,247 A | 6/1992 | Palmer et al. |
| 4,917,800 A | 4/1990 | Lonsdale et al. | 5,130,009 A | 7/1992 | Marsoner et al. |
| 4,919,141 A | 4/1990 | Zier et al. | 5,133,856 A | 7/1992 | Yamaguchi et al. |
| 4,919,767 A | 4/1990 | Vadgama et al. | 5,134,391 A | 7/1992 | Okada |
| 4,920,969 A | 5/1990 | Suzuki | 5,135,003 A | 8/1992 | Souma |
| 4,920,977 A | 5/1990 | Haynes | 5,139,023 A | 8/1992 | Stanley et al. |
| 4,923,586 A | 5/1990 | Katayama et al. | 5,140,393 A | 8/1992 | Hijikihigawa et al. |
| 4,925,268 A | 5/1990 | Iyer et al. | 5,141,868 A | 8/1992 | Shanks et al. |
| 4,927,516 A | 5/1990 | Yamaguchi et al. | 5,161,532 A | 11/1992 | Joseph |
| 4,931,795 A | 6/1990 | Gord | 5,165,407 A | 11/1992 | Wilson et al. |
| 4,934,369 A | 6/1990 | Maxwell | 5,168,046 A | 12/1992 | Hamamoto et al. |
| 4,935,105 A | 6/1990 | Churchouse | 5,174,291 A | 12/1992 | Schoonen et al. |
| 4,935,345 A | 6/1990 | Guilbeau et al. | 5,176,644 A | 1/1993 | Srisathapat et al. |
| 4,936,956 A | 6/1990 | Wrighton | 5,176,662 A | 1/1993 | Bartholomew et al. |
| 4,938,860 A | 7/1990 | Wogoman | 5,182,707 A | 1/1993 | Cooper et al. |
| 4,942,127 A | 7/1990 | Wada et al. | 5,184,359 A | 2/1993 | Tsukamura et al. |
| 4,944,299 A | 7/1990 | Silvian | 5,185,256 A | 2/1993 | Nankai et al. |
| 4,945,045 A | 7/1990 | Forrest et al. | 5,190,041 A | 3/1993 | Palti |
| 4,950,378 A | 8/1990 | Nagata | 5,192,415 A | 3/1993 | Yoshioka et al. |
| 4,953,552 A | 9/1990 | DeMarzo | 5,192,416 A | 3/1993 | Wang et al. |
| 4,954,129 A | 9/1990 | Giuliani et al. | 5,193,539 A | 3/1993 | Schulman et al. |
| 4,957,115 A | 9/1990 | Selker | 5,193,540 A | 3/1993 | Schulman et al. |
| 4,958,632 A | 9/1990 | Duggan | 5,197,322 A | 3/1993 | Indravudh |
| 4,968,400 A | 11/1990 | Shimomura et al. | 5,198,367 A | 3/1993 | Aizawa et al. |
| 4,969,468 A | 11/1990 | Byers et al. | 5,200,051 A | 4/1993 | Cozzette et al. |
| 4,970,145 A | 11/1990 | Bennetto et al. | 5,202,261 A | 4/1993 | Musho et al. |
| 4,974,929 A | 12/1990 | Curry | 5,205,920 A | 4/1993 | Oyama et al. |
| 4,979,509 A | 12/1990 | Hakky | 5,206,145 A | 4/1993 | Cattell |
| 4,986,271 A | 1/1991 | Wilkins | 5,208,154 A | 5/1993 | Weaver et al. |
| 4,990,845 A | 2/1991 | Gord | 5,209,229 A | 5/1993 | Gilli |
| 4,991,582 A | 2/1991 | Byers et al. | 5,215,887 A | 6/1993 | Saito |
| 4,994,068 A | 2/1991 | Hufnagie | 5,216,597 A | 6/1993 | Beckers |
| 4,994,167 A | 2/1991 | Shults et al. | 5,217,442 A | 6/1993 | Davis |
| 4,995,402 A | 2/1991 | Smith et al. | 5,217,595 A | 6/1993 | Smith et al. |
| 5,001,054 A | 3/1991 | Wagner | 5,227,042 A | 7/1993 | Zawodzinski et al. |
| 5,002,054 A | 3/1991 | Ash et al. | 5,229,282 A | 7/1993 | Yoshioka et al. |
| 5,007,427 A | 4/1991 | Suzuki et al. | 5,246,867 A | 9/1993 | Lakowicz et al. |
| 5,016,172 A | 5/1991 | Dessertine | 5,250,439 A | 10/1993 | Musho et al. |
| 5,016,201 A | 5/1991 | Bryan et al. | 5,251,126 A | 10/1993 | Kahn et al. |
| 5,019,974 A | 5/1991 | Beckers | 5,257,971 A | 11/1993 | Lord et al. |
| 5,034,192 A | 7/1991 | Wrighton et al. | 5,257,980 A | 11/1993 | Van Antwerp et al. |
| 5,035,860 A | 7/1991 | Kleingeld et al. | 5,261,401 A | 11/1993 | Baker et al. |
| 5,036,860 A | 8/1991 | Leigh et al. | 5,262,035 A | 11/1993 | Gregg et al. |
| 5,036,861 A | 8/1991 | Sembrowich et al. | 5,262,305 A | 11/1993 | Heller et al. |
| 5,037,527 A | 8/1991 | Hayashi et al. | 5,264,103 A | 11/1993 | Yoshioka et al. |
| 5,049,487 A | 9/1991 | Phillips et al. | 5,264,104 A | 11/1993 | Gregg et al. |
| 5,050,612 A | 9/1991 | Matsumura | 5,264,106 A | 11/1993 | McAleer et al. |
| 5,055,171 A | 10/1991 | Peck | 5,265,888 A | 11/1993 | Yamamoto et al. |
| 5,058,592 A | 10/1991 | Whisler | 5,266,179 A | 11/1993 | Nankai et al. |
| 5,063,081 A | 11/1991 | Cozzette et al. | 5,269,212 A | 12/1993 | Peters et al. |
| 5,068,536 A | 11/1991 | Rosenthal | 5,271,815 A | 12/1993 | Wong |
| 5,070,535 A | 12/1991 | Hochmair et al. | 5,272,060 A | 12/1993 | Hamamoto et al. |
| 5,073,500 A | 12/1991 | Saito et al. | 5,275,159 A | 1/1994 | Griebel |
| 5,077,476 A | 12/1991 | Rosenthal | 5,278,079 A | 1/1994 | Gubinski et al. |
| 5,078,854 A | 1/1992 | Burgess et al. | 5,279,294 A | 1/1994 | Anderson et al. |

| | | | | | | |
|---|---|---|---|---|---|---|
| 5,282,950 A | 2/1994 | Dietze et al. | | 5,482,473 A | 1/1996 | Lord et al. |
| 5,284,156 A | 2/1994 | Schramm et al. | | 5,484,404 A | 1/1996 | Schulman et al. |
| 5,285,792 A | 2/1994 | Sjoquist et al. | | 5,487,751 A | 1/1996 | Radons et al. |
| 5,286,362 A | 2/1994 | Hoenes et al. | | 5,491,474 A | 2/1996 | Suni et al. |
| 5,286,364 A | 2/1994 | Yacynych et al. | | 5,494,562 A | 2/1996 | Maley et al. |
| 5,288,636 A | 2/1994 | Pollmann et al. | | 5,496,453 A | 3/1996 | Uenoyama et al. |
| 5,291,887 A | 3/1994 | Stanley et al. | | 5,497,772 A | 3/1996 | Schulman et al. |
| 5,293,546 A | 3/1994 | Tadros et al. | | 5,501,956 A | 3/1996 | Wada et al. |
| 5,299,571 A | 4/1994 | Mastrototaro | | 5,505,709 A | 4/1996 | Funderburk |
| 5,304,468 A | 4/1994 | Phillips et al. | | 5,505,713 A | 4/1996 | Van Antwerp et al. |
| 5,307,263 A | 4/1994 | Brown | | 5,507,288 A | 4/1996 | Bocker et al. |
| 5,309,919 A | 5/1994 | Snell et al. | | 5,508,171 A | 4/1996 | Walling et al. |
| 5,310,885 A | 5/1994 | Maier et al. | | 5,509,410 A | 4/1996 | Hill et al. |
| 5,320,098 A | 6/1994 | Davidson | | 5,514,103 A | 5/1996 | Srisathapat et al. |
| 5,320,725 A | 6/1994 | Gregg et al. | | 5,514,253 A | 5/1996 | Davis et al. |
| 5,322,063 A | 6/1994 | Allen et al. | | 5,518,006 A | 5/1996 | Mawhirt et al. |
| 5,324,303 A | 6/1994 | Strong et al. | | 5,520,787 A | 5/1996 | Hanagan et al. |
| 5,324,316 A | 6/1994 | Schulman et al. | | 5,522,865 A | 6/1996 | Schulman et al. |
| 5,326,449 A | 7/1994 | Cunningham | | 5,525,511 A | 6/1996 | D'Costa |
| 5,337,258 A | 8/1994 | Dennis | | 5,526,120 A | 6/1996 | Jina et al. |
| 5,337,747 A | 8/1994 | Neftel | | 5,527,307 A | 6/1996 | Srisathapat et al. |
| 5,340,722 A | 8/1994 | Wolfbeis et al. | | 5,529,676 A | 6/1996 | Maley et al. |
| 5,342,789 A | 8/1994 | Chick et al. | | 5,531,878 A | 7/1996 | Vadgama et al. |
| 5,352,348 A | 10/1994 | Young et al. | | 5,538,511 A | 7/1996 | Van Antwerp et al. |
| 5,356,348 A | 10/1994 | Bellio et al. | | 5,545,152 A | 8/1996 | Funderburk et al. |
| 5,356,786 A | 10/1994 | Heller et al. | | 5,545,191 A | 8/1996 | Mann et al. |
| 5,358,514 A | 10/1994 | Schulman et al. | | 5,549,113 A | 8/1996 | Halleck et al. |
| 5,364,797 A | 11/1994 | Olson et al. | | 5,549,115 A | 8/1996 | Morgan et al. |
| 5,366,609 A | 11/1994 | White et al. | | 5,552,027 A | 9/1996 | Birkle et al. |
| 5,368,028 A | 11/1994 | Palti | | 5,554,166 A | 9/1996 | Lange et al. |
| 5,370,622 A | 12/1994 | Livingston et al. | | 5,556,524 A | 9/1996 | Albers |
| 5,371,687 A | 12/1994 | Holmes, II et al. | | 5,560,357 A | 10/1996 | Faupei et al. |
| 5,371,734 A * | 12/1994 | Fischer ............... 455/518 | | 5,562,713 A | 10/1996 | Silvian |
| 5,372,133 A | 12/1994 | Hogen Esch | | 5,565,085 A | 10/1996 | Ikeda et al. |
| 5,376,070 A | 12/1994 | Purvis et al. | | 5,567,302 A | 10/1996 | Song et al. |
| 5,376,251 A | 12/1994 | Kaneko et al. | | 5,568,806 A | 10/1996 | Cheney, II et al. |
| 5,377,258 A | 12/1994 | Bro | | 5,569,186 A | 10/1996 | Lord et al. |
| 5,378,628 A | 1/1995 | Gratzel et al. | | 5,569,212 A | 10/1996 | Brown |
| 5,379,238 A | 1/1995 | Stark | | 5,573,647 A | 11/1996 | Maley et al. |
| 5,380,422 A | 1/1995 | Negishis et al. | | 5,575,895 A | 11/1996 | Ikeda et al. |
| 5,382,346 A | 1/1995 | Uenoyama et al. | | 5,580,527 A | 12/1996 | Bell et al. |
| 5,387,327 A | 2/1995 | Khan | | 5,580,794 A | 12/1996 | Allen |
| 5,390,671 A | 2/1995 | Lord et al. | | 5,582,184 A | 12/1996 | Erickson et al. |
| 5,391,250 A | 2/1995 | Cheney, II et al. | | 5,582,697 A | 12/1996 | Ikeda et al. |
| 5,393,903 A | 2/1995 | Gratzel et al. | | 5,582,698 A | 12/1996 | Flaherty et al. |
| 5,395,504 A | 3/1995 | Saurer et al. | | 5,584,813 A | 12/1996 | Livingston et al. |
| 5,399,823 A | 3/1995 | McCusker | | 5,586,553 A | 12/1996 | Halli et al. |
| 5,400,782 A | 3/1995 | Beaubiah | | 5,589,326 A | 12/1996 | Deng et al. |
| 5,408,999 A | 4/1995 | Singh et al. | | 5,593,852 A | 1/1997 | Heller et al. |
| 5,410,471 A | 4/1995 | Alyfuku et al. | | 5,594,906 A | 1/1997 | Holmes, II et al. |
| 5,410,474 A | 4/1995 | Fox | | 5,596,150 A | 1/1997 | Arndy et al. |
| 5,411,647 A | 5/1995 | Johnson et al. | | 5,596,994 A | 1/1997 | Bro |
| 5,413,690 A | 5/1995 | Kost et al. | | 5,601,435 A | 2/1997 | Quy |
| 5,422,246 A | 6/1995 | Koopal et al. | | 5,601,694 A | 2/1997 | Maley et al. |
| 5,431,160 A | 7/1995 | Wilkins | | 5,605,152 A | 2/1997 | Slate et al. |
| 5,431,691 A | 7/1995 | Snell et al. | | 5,611,900 A | 3/1997 | Worden et al. |
| 5,431,921 A | 7/1995 | Thombre | | 5,615,671 A | 4/1997 | Schoonen et al. |
| 5,433,710 A | 7/1995 | Van Antwerp et al. | | 5,616,222 A | 4/1997 | Maley et al. |
| 5,437,973 A | 8/1995 | Vadgama et al. | | 5,617,851 A | 4/1997 | Lipkovker |
| 5,437,999 A | 8/1995 | Diebold et al. | | 5,623,925 A | 4/1997 | Swenson et al. |
| 5,445,611 A | 8/1995 | Eppstein et al. | | 5,628,309 A | 5/1997 | Brown |
| 5,445,920 A | 8/1995 | Saito | | 5,628,310 A | 5/1997 | Rao et al. |
| 5,456,692 A | 10/1995 | Smith, Jr. et al. | | 5,628,890 A | 5/1997 | Carter et al. |
| 5,456,940 A | 10/1995 | Funderburk | | 5,629,981 A | 5/1997 | Nerlikar |
| 5,458,140 A | 10/1995 | Eppstein et al. | | 5,637,095 A | 6/1997 | Nason et al. |
| 5,460,618 A | 10/1995 | Harreld | | 5,640,764 A | 6/1997 | Strojnik |
| 5,462,525 A | 10/1995 | Srisathapat et al. | | 5,640,954 A | 6/1997 | Pfeiffer et al. |
| 5,462,645 A | 10/1995 | Albery et al. | | 5,643,212 A | 7/1997 | Coutre et al. |
| 5,466,218 A | 11/1995 | Srisathapat et al. | | 5,647,853 A | 7/1997 | Feldmann et al. |
| 5,469,846 A | 11/1995 | Khan | | 5,650,062 A | 7/1997 | Ikeda et al. |
| 5,472,317 A | 12/1995 | Field et al. | | 5,651,767 A | 7/1997 | Schulman et al. |
| 5,476,460 A | 12/1995 | Montalvo | | 5,651,869 A | 7/1997 | Yoshioka et al. |
| 5,477,855 A | 12/1995 | Schindler et al. | | 5,660,163 A | 8/1997 | Schulman et al. |

| | | | | | |
|---|---|---|---|---|---|
| 5,665,065 A | 9/1997 | Colman et al. | 5,854,078 A | 12/1998 | Asher et al. |
| 5,667,983 A | 9/1997 | Abel et al. | 5,854,189 A | 12/1998 | Kruse et al. |
| 5,670,031 A | 9/1997 | Hintsche et al. | 5,857,967 A | 1/1999 | Frid et al. |
| 5,678,571 A | 10/1997 | Brown | 5,857,983 A | 1/1999 | Douglas et al. |
| 5,679,690 A | 10/1997 | Andre et al. | 5,860,917 A | 1/1999 | Comanor et al. |
| 5,680,858 A | 10/1997 | Hansen et al. | 5,872,713 A | 2/1999 | Douglas et al. |
| 5,682,233 A | 10/1997 | Brinda | 5,876,484 A | 3/1999 | Raskin et al. |
| 5,686,717 A | 11/1997 | Knowles et al. | 5,879,163 A | 3/1999 | Brown et al. |
| 5,695,623 A | 12/1997 | Michel et al. | 5,879,311 A | 3/1999 | Duchon et al. |
| 5,695,949 A | 12/1997 | Galen et al. | 5,880,829 A | 3/1999 | Kauhaniemi et al. |
| 5,701,894 A | 12/1997 | Cherry et al. | 5,882,494 A | 3/1999 | Van Antwerp |
| 5,704,922 A | 1/1998 | Brown | 5,885,211 A | 3/1999 | Eppstein et al. |
| 5,707,502 A | 1/1998 | McCaffrey et al. | 5,887,133 A | 3/1999 | Brown et al. |
| 5,708,247 A | 1/1998 | McAleer et al. | 5,897,493 A | 4/1999 | Brown |
| 5,710,630 A | 1/1998 | Essenpreis et al. | 5,898,025 A | 4/1999 | Burg et al. |
| 5,711,001 A | 1/1998 | Bussan et al. | 5,899,855 A | 5/1999 | Brown |
| 5,711,297 A | 1/1998 | Iliff et al. | 5,913,310 A | 6/1999 | Brown |
| 5,711,861 A | 1/1998 | Ward et al. | 5,917,346 A | 6/1999 | Gord |
| 5,711,862 A | 1/1998 | Sakoda et al. | 5,918,603 A | 7/1999 | Brown |
| 5,711,868 A | 1/1998 | Maley et al. | 5,925,021 A | 7/1999 | Castellano et al. |
| 5,718,234 A * | 2/1998 | Warden et al. ............... 600/300 | 5,931,791 A | 8/1999 | Saltzstein et al. |
| 5,720,733 A | 2/1998 | Brown | 5,933,136 A | 8/1999 | Brown |
| 5,720,862 A | 2/1998 | Hamamoto et al. | 5,940,801 A | 8/1999 | Brown |
| 5,721,783 A | 2/1998 | Anderson | 5,942,979 A | 8/1999 | Luppino |
| 5,722,397 A | 3/1998 | Eppstein | 5,945,345 A | 8/1999 | Blatt et al. |
| 5,727,548 A | 3/1998 | Hill et al. | 5,947,921 A | 9/1999 | Johnson et al. |
| 5,730,124 A | 3/1998 | Yamauchi | 5,948,512 A | 9/1999 | Kubota et al. |
| 5,730,654 A | 3/1998 | Brown | 5,950,632 A | 9/1999 | Reber et al. |
| 5,735,273 A | 4/1998 | Kurnik et al. | 5,951,300 A | 9/1999 | Brown |
| 5,735,285 A | 4/1998 | Albert et al. | 5,951,492 A | 9/1999 | Douglas et al. |
| 5,741,211 A | 4/1998 | Renirie et al. | 5,951,521 A | 9/1999 | Mastrototaro et al. |
| 5,741,688 A | 4/1998 | Oxenboll et al. | 5,951,836 A | 9/1999 | McAleer et al. |
| 5,746,217 A | 5/1998 | Erickson et al. | 5,954,643 A | 9/1999 | Van Antwerp |
| 5,750,926 A | 5/1998 | Schulman et al. | 5,954,685 A | 9/1999 | Tierney |
| 5,770,028 A | 6/1998 | Maley et al. | 5,954,700 A | 9/1999 | Kovelman |
| 5,771,001 A | 6/1998 | Cobb | 5,956,501 A | 9/1999 | Brown |
| 5,771,890 A | 6/1998 | Tamada | 5,957,854 A | 9/1999 | Besson et al. |
| 5,772,586 A | 6/1998 | Heinonen et al. | 5,957,890 A | 9/1999 | Mann et al. |
| 5,777,060 A | 7/1998 | Van Antwerp | 5,957,958 A | 9/1999 | Schulman et al. |
| 5,779,665 A | 7/1998 | Mastrototaro et al. | 5,960,403 A | 9/1999 | Brown |
| 5,782,814 A | 7/1998 | Brown et al. | 5,961,451 A | 10/1999 | Reber et al. |
| 5,785,681 A | 7/1998 | Indravudh | 5,964,993 A | 10/1999 | Blubaugh, Jr. et al. |
| 5,786,439 A | 7/1998 | Van Antwerp et al. | 5,965,380 A | 10/1999 | Heller et al. |
| 5,786,584 A | 7/1998 | Button et al. | 5,968,839 A | 10/1999 | Blatt et al. |
| 5,788,678 A | 8/1998 | Van Antwerp | 5,971,922 A | 10/1999 | Arita et al. |
| 5,791,344 A | 8/1998 | Schulman et al. | 5,971,941 A | 10/1999 | Simons et al. |
| 5,792,117 A | 8/1998 | Brown | 5,974,124 A | 10/1999 | Schlueter, Jr. et al. |
| 5,800,420 A | 9/1998 | Gross et al. | 5,977,476 A | 11/1999 | Guha et al. |
| 5,804,048 A | 9/1998 | Wong et al. | 5,981,294 A | 11/1999 | Blatt et al. |
| 5,806,517 A | 9/1998 | Gerhardt et al. | 5,989,409 A | 11/1999 | Kurnik et al. |
| 5,807,315 A | 9/1998 | Van Antwerp et al. | 5,994,476 A | 11/1999 | Shin et al. |
| 5,807,375 A | 9/1998 | Gross et al. | 5,995,860 A | 11/1999 | Sun et al. |
| 5,814,599 A | 9/1998 | Mitragotri et al. | 5,997,476 A | 12/1999 | Brown |
| 5,820,551 A | 10/1998 | Hill et al. | 5,999,848 A | 12/1999 | Gord et al. |
| 5,820,570 A | 10/1998 | Erickson et al. | 5,999,849 A | 12/1999 | Gord et al. |
| 5,820,622 A | 10/1998 | Gross et al. | 6,001,067 A | 12/1999 | Shults et al. |
| 5,822,715 A | 10/1998 | Worthington et al. | 6,002,954 A | 12/1999 | Van Antwerp et al. |
| 5,825,488 A | 10/1998 | Kohl et al. | 6,002,961 A | 12/1999 | Mitragotri et al. |
| 5,827,179 A | 10/1998 | Lichter et al. | 6,004,441 A | 12/1999 | Fujiwara et al. |
| 5,827,183 A | 10/1998 | Kurnik et al. | 6,011,984 A | 1/2000 | Van Antwerp et al. |
| 5,827,184 A | 10/1998 | Netherly et al. | 6,014,577 A | 1/2000 | Henning et al. |
| 5,828,943 A | 10/1998 | Brown | 6,018,678 A | 1/2000 | Mitragotri et al. |
| 5,830,341 A | 11/1998 | Gilmartin | 6,023,629 A | 2/2000 | Tamada |
| 5,832,448 A | 11/1998 | Brown | 6,024,699 A | 2/2000 | Surwit et al. |
| 5,834,224 A | 11/1998 | Ruger et al. | 6,026,320 A | 2/2000 | Carlson et al. |
| 5,837,454 A | 11/1998 | Cozzette et al. | 6,027,459 A | 2/2000 | Shain et al. |
| 5,837,546 A | 11/1998 | Allen et al. | 6,027,692 A | 2/2000 | Galen et al. |
| 5,840,020 A | 11/1998 | Heinonen et al. | 6,032,059 A | 2/2000 | Henning et al. |
| 5,842,983 A | 12/1998 | Abel et al. | 6,032,199 A | 2/2000 | Lim et al. |
| 5,843,140 A | 12/1998 | Strojnik | 6,033,866 A | 3/2000 | Guo et al. |
| 5,846,702 A | 12/1998 | Deng et al. | 6,035,237 A | 3/2000 | Schulman et al. |
| 5,846,744 A | 12/1998 | Athey et al. | 6,040,194 A | 3/2000 | Chick et al. |
| 5,851,197 A | 12/1998 | Marano et al. | 6,041,253 A | 3/2000 | Kost et al. |

| | | | | | | |
|---|---|---|---|---|---|---|
| 6,043,437 | A | 3/2000 | Schulman et al. | 6,233,471 B1 | 5/2001 | Berner et al. |
| 6,049,727 | A | 4/2000 | Crothall | 6,233,539 B1 | 5/2001 | Brown |
| 6,056,718 | A | 5/2000 | Funderburk et al. | 6,239,925 B1 | 5/2001 | Ardrey et al. |
| 6,063,459 | A | 5/2000 | Velte | 6,241,862 B1 | 6/2001 | McAleer et al. |
| 6,066,243 | A | 5/2000 | Anderson et al. | 6,246,330 B1 | 6/2001 | Nielsen |
| 6,067,474 | A | 5/2000 | Schulman et al. | 6,246,992 B1 | 6/2001 | Brown |
| 6,068,615 | A | 5/2000 | Brown et al. | 6,248,065 B1 | 6/2001 | Brown |
| 6,071,249 | A | 6/2000 | Cunningham et al. | 6,248,067 B1 | 6/2001 | Causey, III et al. |
| 6,071,251 | A | 6/2000 | Cunningham et al. | 6,248,093 B1 | 6/2001 | Moberg |
| 6,071,294 | A | 6/2000 | Simons et al. | 6,251,260 B1 | 6/2001 | Heller et al. |
| 6,071,391 | A | 6/2000 | Gotoh et al. | 6,252,032 B1 | 6/2001 | Van Antwerp et al. |
| 6,081,736 | A | 6/2000 | Colvin et al. | 6,253,804 B1 | 7/2001 | Safabash |
| 6,083,710 | A | 7/2000 | Heller et al. | 6,254,586 B1 | 7/2001 | Mann et al. |
| 6,088,608 | A | 7/2000 | Schulman et al. | 6,256,643 B1 | 7/2001 | Cork et al. |
| 6,091,975 | A | 7/2000 | Daddona et al. | 6,259,587 B1 | 7/2001 | Sheldon et al. |
| 6,091,976 | A | 7/2000 | Pfeiffer et al. | 6,259,937 B1 | 7/2001 | Schulman et al. |
| 6,093,156 | A | 7/2000 | Cunningham et al. | 6,260,022 B1 | 7/2001 | Brown |
| 6,093,167 | A | 7/2000 | Houben et al. | 6,266,645 B1 | 7/2001 | Simpson |
| 6,093,172 | A | 7/2000 | Funderburk et al. | 6,267,724 B1 | 7/2001 | Taylor |
| 6,097,831 | A | 8/2000 | Wieck et al. | 6,268,161 B1 | 7/2001 | Han et al. |
| 6,099,484 | A | 8/2000 | Douglas et al. | 6,270,445 B1 | 8/2001 | Dean, Jr. et al. |
| 6,101,478 | A | 8/2000 | Brown | 6,272,364 B1 | 8/2001 | Kurnik |
| 6,103,033 | A | 8/2000 | Say et al. | 6,275,717 B1 | 8/2001 | Gross et al. |
| 6,106,780 | A | 8/2000 | Douglas et al. | 6,280,416 B1 | 8/2001 | Van Antwerp et al. |
| 6,110,148 | A | 8/2000 | Brown et al. | 6,280,587 B1 | 8/2001 | Matsumoto |
| 6,110,152 | A | 8/2000 | Kovelman | 6,281,006 B1 | 8/2001 | Heller et al. |
| 6,113,578 | A | 9/2000 | Brown | 6,283,943 B1 | 9/2001 | Dy et al. |
| 6,119,028 | A | 9/2000 | Schulman et al. | 6,284,126 B1 | 9/2001 | Kurnik et al. |
| 6,120,676 | A | 9/2000 | Heller et al. | 6,284,478 B1 | 9/2001 | Heller et al. |
| 6,121,009 | A | 9/2000 | Heller et al. | 6,293,925 B1 | 9/2001 | Safabash et al. |
| 6,122,351 | A | 9/2000 | Schlueter, Jr. et al. | 6,294,281 B1 | 9/2001 | Heller |
| 6,125,978 | A | 10/2000 | Ando et al. | 6,295,463 B1 | 9/2001 | Stenzler |
| 6,134,461 | A | 10/2000 | Say et al. | 6,295,506 B1 | 9/2001 | Heinonen et al. |
| 6,134,504 | A | 10/2000 | Douglas et al. | 6,298,254 B2 | 10/2001 | Tamada |
| 6,139,718 | A | 10/2000 | Kurnik et al. | 6,299,578 B1 | 10/2001 | Kurnik et al. |
| 6,141,573 | A | 10/2000 | Kurnik et al. | 6,299,757 B1 | 10/2001 | Feldman et al. |
| 6,142,939 | A | 11/2000 | Eppstein et al. | 6,301,499 B1 | 10/2001 | Carlson et al. |
| 6,143,164 | A | 11/2000 | Heller et al. | 6,304,766 B1 | 10/2001 | Colvin, Jr. et al. |
| 6,144,837 | A | 11/2000 | Quy | 6,309,351 B1 | 10/2001 | Kurnik et al. |
| 6,144,869 | A | 11/2000 | Berner et al. | 6,309,884 B1 | 10/2001 | Cooper et al. |
| 6,144,922 | A | 11/2000 | Douglas et al. | 6,315,721 B2 | 11/2001 | Schulman et al. |
| 6,148,094 | A | 11/2000 | Kinsella | 6,319,540 B1 | 11/2001 | Van Antwerp et al. |
| 6,150,128 | A | 11/2000 | Uretsky | 6,326,160 B1 | 12/2001 | Dunn et al. |
| 6,151,586 | A | 11/2000 | Brown | 6,329,161 B1 | 12/2001 | Heller et al. |
| 6,153,062 | A | 11/2000 | Saito et al. | 6,329,929 B1 | 12/2001 | Weijand et al. |
| 6,153,069 | A | 11/2000 | Pottgen et al. | 6,330,426 B2 | 12/2001 | Brown et al. |
| 6,159,147 | A | 12/2000 | Lichter et al. | 6,330,464 B1 | 12/2001 | Colvin, Jr. et al. |
| 6,161,095 | A | 12/2000 | Brown | 6,331,518 B2 | 12/2001 | Hemm et al. |
| 6,162,611 | A | 12/2000 | Heller et al. | 6,334,778 B1 | 1/2002 | Brown |
| 6,162,639 | A | 12/2000 | Douglas | 6,336,900 B1 | 1/2002 | Alleckson et al. |
| 6,167,362 | A | 12/2000 | Brown et al. | 6,338,790 B1 | 1/2002 | Feldman et al. |
| 6,168,563 | B1 | 1/2001 | Brown | 6,340,421 B1 | 1/2002 | Vachon et al. |
| 6,170,318 | B1 | 1/2001 | Lewis | 6,341,232 B1 | 1/2002 | Conn et al. |
| 6,175,752 | B1 | 1/2001 | Say et al. | 6,356,776 B1 | 3/2002 | Berner et al. |
| 6,180,416 | B1 | 1/2001 | Kurnik et al. | 6,360,888 B1 | 3/2002 | McIvor et al. |
| 6,186,145 | B1 | 2/2001 | Brown | 6,366,793 B1 | 4/2002 | Bell et al. |
| 6,192,891 | B1 | 2/2001 | Gravel et al. | 6,366,794 B1 | 4/2002 | Moussy et al. |
| 6,193,873 | B1 | 2/2001 | Ohara et al. | 6,368,141 B1 | 4/2002 | Van Antwerp et al. |
| 6,196,970 | B1 | 3/2001 | Brown | 6,368,274 B1 | 4/2002 | Van Antwerp et al. |
| 6,198,957 | B1 | 3/2001 | Green | 6,370,410 B2 | 4/2002 | Kurnik et al. |
| 6,201,979 | B1 | 3/2001 | Kurnik et al. | 6,379,301 B1 | 4/2002 | Worthington et al. |
| 6,201,980 | B1 | 3/2001 | Darrow et al. | 6,383,767 B1 | 5/2002 | Polak |
| 6,206,841 | B1 | 3/2001 | Cunningham et al. | 6,387,048 B1 | 5/2002 | Schulman et al. |
| 6,207,400 | B1 | 3/2001 | Kwon | 6,391,643 B1 | 5/2002 | Chen et al. |
| 6,208,894 | B1 | 3/2001 | Schulman et al. | 6,398,562 B1 | 6/2002 | Butler et al. |
| 6,210,272 | B1 | 4/2001 | Brown | 6,405,066 B1 | 6/2002 | Essenpreis et al. |
| 6,210,976 | B1 | 4/2001 | Sabbadini | 6,413,393 B1 | 7/2002 | Van Antwerp et al. |
| 6,212,416 | B1 | 4/2001 | Ward et al. | 6,418,332 B1 | 7/2002 | Mastrototaro et al. |
| 6,219,565 | B1 | 4/2001 | Cupp et al. | 6,424,847 B1 | 7/2002 | Mastrototaro et al. |
| 6,219,574 | B1 | 4/2001 | Cormier et al. | 6,427,088 B1 | 7/2002 | Bowman, IV et al. |
| 6,224,745 | B1 | 5/2001 | Baltruschat | 6,434,409 B1 | 8/2002 | Pfeiffer et al. |
| 6,232,130 | B1 | 5/2001 | Wolf | 6,438,414 B1 | 8/2002 | Conn et al. |
| 6,232,370 | B1 | 5/2001 | Kubota et al. | 6,440,068 B1 | 8/2002 | Brown et al. |

| Patent No. | Date | Inventor |
|---|---|---|
| 6,441,747 B1 * | 8/2002 | Khair et al. .................. 128/903 |
| 6,442,637 B1 | 8/2002 | Hawkins et al. |
| 6,443,942 B2 | 9/2002 | Van Antwerp et al. |
| 6,454,710 B1 | 9/2002 | Ballerstadt et al. |
| 6,462,162 B2 | 10/2002 | Van Antwerp et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,472,122 B1 | 10/2002 | Schulman et al. |
| 6,475,750 B1 | 11/2002 | Han et al. |
| 6,477,395 B2 | 11/2002 | Schulman et al. |
| 6,478,736 B1 | 11/2002 | Mault |
| 6,480,730 B2 | 11/2002 | Darrow et al. |
| 6,482,158 B2 | 11/2002 | Mault |
| 6,482,604 B2 | 11/2002 | Kwon |
| 6,484,045 B1 | 11/2002 | Holker et al. |
| 6,485,138 B1 | 11/2002 | Kubota et al. |
| 6,494,830 B1 | 12/2002 | Wessel |
| 6,496,728 B2 | 12/2002 | Li et al. |
| 6,505,059 B1 | 1/2003 | Kollias et al. |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 * | 2/2003 | Stark et al. .................. 128/903 |
| 6,520,326 B2 | 2/2003 | McIvor et al. |
| 6,529,755 B2 | 3/2003 | Kurnik et al. |
| 6,529,772 B2 | 3/2003 | Carlson et al. |
| 6,530,915 B1 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,571,200 B1 | 5/2003 | Mault |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,587,705 B1 | 7/2003 | Kim et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,678 B2 | 8/2003 | Kwon et al. |
| 6,602,909 B2 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,612,306 B1 | 9/2003 | Mault |
| 6,615,078 B1 | 9/2003 | Burson et al. |
| 6,618,603 B2 | 9/2003 | Varalli et al. |
| 6,620,106 B2 | 9/2003 | Mault |
| 6,627,058 B1 | 9/2003 | Chan |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 * | 11/2003 | Causey et al. .................. 600/300 |
| 6,642,015 B2 | 11/2003 | Vachon et al. |
| 6,645,142 B2 | 11/2003 | Braig et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,693,069 B2 | 2/2004 | Kober et al. |
| 6,694,158 B2 | 2/2004 | Polak |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,704,587 B1 | 3/2004 | Kumar et al. |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,736,777 B2 | 5/2004 | Kim et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,743,635 B2 | 6/2004 | Neel et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,771,995 B2 | 8/2004 | Kurnik et al. |
| 6,773,563 B2 | 8/2004 | Matsumoto |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,500 B1 | 2/2005 | Hoss et al. |
| 6,852,694 B2 | 2/2005 | Van Antwerp et al. |

| Patent No. | Date | Inventor |
|---|---|---|
| 6,853,854 B1 | 2/2005 | Proniewicz et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,899,683 B2 | 5/2005 | Mault et al. |
| 6,899,684 B2 | 5/2005 | Mault et al. |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,936,006 B2 | 8/2005 | Sabra |
| 6,936,029 B2 | 8/2005 | Mann et al. |
| 6,940,590 B2 | 9/2005 | Colvin, Jr. et al. |
| 6,941,163 B2 | 9/2005 | Ford et al. |
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,968,294 B2 | 11/2005 | Gutta et al. |
| 6,968,375 B1 | 11/2005 | Brown |
| 6,974,437 B2 | 12/2005 | Lebel et al. |
| 6,978,182 B2 | 12/2005 | Mazar et al. |
| 6,979,326 B2 | 12/2005 | Mann et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,029,444 B2 | 4/2006 | Shin et al. |
| 7,039,810 B1 | 5/2006 | Nichols |
| 7,041,468 B2 | 5/2006 | Drucker et al. |
| 7,049,277 B2 | 5/2006 | Bragulla et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,109,878 B2 | 9/2006 | Mann et al. |
| 7,110,803 B2 | 9/2006 | Shults et al. |
| 7,113,821 B1 | 9/2006 | Sun et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,137,964 B2 | 11/2006 | Flaherty |
| 7,150,975 B2 | 12/2006 | Tamada et al. |
| 7,163,511 B2 | 1/2007 | Conn et al. |
| 7,171,274 B2 | 1/2007 | Starkweather et al. |
| 7,183,068 B2 | 2/2007 | Burson et al. |
| 7,183,102 B2 | 2/2007 | Monfre et al. |
| 7,187,528 B2 | 3/2007 | Talbot et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,226,978 B2 | 6/2007 | Tapsak et al. |
| 7,228,163 B2 | 6/2007 | Ackerman |
| 7,233,817 B2 | 6/2007 | Yen |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,295,867 B2 | 11/2007 | Berner et al. |
| 7,310,544 B2 | 12/2007 | Brister et al. |
| 7,318,816 B2 | 1/2008 | Bobroff et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2001/0051768 A1 | 12/2001 | Schulman et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0016530 A1 | 2/2002 | Brown |
| 2002/0019022 A1 | 2/2002 | Dunn et al. |
| 2002/0019586 A1 | 2/2002 | Teller et al. |

| | | | | | |
|---|---|---|---|---|---|
| 2002/0019748 A1 | 2/2002 | Brown | 2003/0199791 A1 | 10/2003 | Boecker et al. |
| 2002/0026937 A1 | 3/2002 | Mault | 2003/0199903 A1 | 10/2003 | Boecker et al. |
| 2002/0027164 A1 | 3/2002 | Mault et al. | 2003/0208110 A1 | 11/2003 | Mault et al. |
| 2002/0028995 A1 | 3/2002 | Mault | 2003/0208113 A1 | 11/2003 | Mault et al. |
| 2002/0040208 A1 | 4/2002 | Flaherty et al. | 2003/0208133 A1 | 11/2003 | Mault |
| 2002/0042090 A1 | 4/2002 | Heller et al. | 2003/0208409 A1 | 11/2003 | Mault |
| 2002/0042561 A1 | 4/2002 | Schulman et al. | 2003/0212364 A1 | 11/2003 | Mann et al. |
| 2002/0047867 A1 | 4/2002 | Mault et al. | 2003/0212379 A1 | 11/2003 | Bylund et al. |
| 2002/0053637 A1 | 5/2002 | Conn et al. | 2003/0217966 A1 | 11/2003 | Tapsak et al. |
| 2002/0062069 A1 | 5/2002 | Mault | 2003/0226695 A1 | 12/2003 | Mault |
| 2002/0063060 A1 | 5/2002 | Gascoyne et al. | 2003/0229514 A2 | 12/2003 | Brown |
| 2002/0068858 A1 | 6/2002 | Braig et al. | 2003/0232370 A1 | 12/2003 | Trifiro |
| 2002/0072858 A1 | 6/2002 | Cheng | 2003/0235817 A1 | 12/2003 | Bartkowiak et al. |
| 2002/0077765 A1 | 6/2002 | Mault | 2004/0010207 A1 | 1/2004 | Flaherty et al. |
| 2002/0077766 A1 | 6/2002 | Mault | 2004/0011671 A1 | 1/2004 | Shults et al. |
| 2002/0081559 A1 | 6/2002 | Brown et al. | 2004/0018486 A1 | 1/2004 | Dunn et al. |
| 2002/0083461 A1 | 6/2002 | Hutcheson et al. | 2004/0039256 A1 | 2/2004 | Kawatahara et al. |
| 2002/0087056 A1 | 7/2002 | Aceti et al. | 2004/0040840 A1 | 3/2004 | Mao et al. |
| 2002/0091312 A1 | 7/2002 | Berner et al. | 2004/0045879 A1 | 3/2004 | Shults et al. |
| 2002/0103425 A1 | 8/2002 | Mault | 2004/0054263 A1 | 3/2004 | Moerman et al. |
| 2002/0107433 A1 | 8/2002 | Mault | 2004/0059201 A1 | 3/2004 | Ginsberg |
| 2002/0107476 A1 | 8/2002 | Mann et al. | 2004/0069164 A1 | 4/2004 | Nakamura et al. |
| 2002/0109600 A1 | 8/2002 | Mault et al. | 2004/0072357 A1 | 4/2004 | Stiene et al. |
| 2002/0119711 A1 | 8/2002 | Van Antwerp et al. | 2004/0073095 A1 | 4/2004 | Causey, III et al. |
| 2002/0124017 A1 | 9/2002 | Mault | 2004/0096959 A1 | 5/2004 | Stiene et al. |
| 2002/0128594 A1 | 9/2002 | Das et al. | 2004/0106858 A1 | 6/2004 | Say et al. |
| 2002/0130042 A1 | 9/2002 | Moerman et al. | 2004/0106859 A1 | 6/2004 | Say et al. |
| 2002/0133378 A1 | 9/2002 | Mault et al. | 2004/0108226 A1 | 6/2004 | Polychronakos et al. |
| 2002/0161286 A1 | 10/2002 | Gerber et al. | 2004/0122353 A1 | 6/2004 | Shahmirian et al. |
| 2002/0161288 A1 | 10/2002 | Shin et al. | 2004/0122489 A1 | 6/2004 | Mazar et al. |
| 2002/0177764 A1 | 11/2002 | Sohrab | 2004/0133164 A1 | 7/2004 | Funderburk et al. |
| 2002/0198513 A1 | 12/2002 | Lebel et al. | 2004/0138588 A1 | 7/2004 | Saikley et al. |
| 2003/0023182 A1 | 1/2003 | Mault et al. | 2004/0153585 A1 | 8/2004 | Kawatahara et al. |
| 2003/0023317 A1 | 1/2003 | Brauker et al. | 2004/0162473 A1 | 8/2004 | Sohrab |
| 2003/0028089 A1 | 2/2003 | Galley et al. | 2004/0164961 A1 | 8/2004 | Bal et al. |
| 2003/0028120 A1 | 2/2003 | Mault et al. | 2004/0167383 A1 | 8/2004 | Kim et al. |
| 2003/0032077 A1 | 2/2003 | Itoh et al. | 2004/0167801 A1 | 8/2004 | Say et al. |
| 2003/0032867 A1 | 2/2003 | Crothall et al. | 2004/0171921 A1 | 9/2004 | Say et al. |
| 2003/0032868 A1 | 2/2003 | Graskov et al. | 2004/0172284 A1 | 9/2004 | Sullivan et al. |
| 2003/0032874 A1 | 2/2003 | Rhodes et al. | 2004/0176913 A1 | 9/2004 | Kawatahara et al. |
| 2003/0040683 A1 | 2/2003 | Rule et al. | 2004/0186362 A1 | 9/2004 | Brauker et al. |
| 2003/0042137 A1 | 3/2003 | Mao et al. | 2004/0193025 A1 | 9/2004 | Steil et al. |
| 2003/0050537 A1 | 3/2003 | Wessel | 2004/0193090 A1 | 9/2004 | Lebel et al. |
| 2003/0050546 A1 | 3/2003 | Desai et al. | 2004/0199059 A1 | 10/2004 | Brauker et al. |
| 2003/0065257 A1 | 4/2003 | Mault et al. | 2004/0202576 A1 | 10/2004 | Aceti et al. |
| 2003/0065273 A1 | 4/2003 | Mault et al. | 2004/0219664 A1 | 11/2004 | Heller et al. |
| 2003/0065274 A1 | 4/2003 | Mault et al. | 2004/0225338 A1 | 11/2004 | Lebel et al. |
| 2003/0065275 A1 | 4/2003 | Mault et al. | 2004/0236200 A1 | 11/2004 | Say et al. |
| 2003/0065308 A1 | 4/2003 | Lebel et al. | 2004/0248204 A1 | 12/2004 | Moerman |
| 2003/0100040 A1 | 5/2003 | Bonnecaze et al. | 2004/0249250 A1 | 12/2004 | McGee et al. |
| 2003/0100821 A1 | 5/2003 | Heller et al. | 2004/0249253 A1 | 12/2004 | Racchini et al. |
| 2003/0105407 A1 | 6/2003 | Pearce et al. | 2004/0249254 A1 | 12/2004 | Racchini et al. |
| 2003/0108976 A1 | 6/2003 | Braig et al. | 2004/0249999 A1 | 12/2004 | Connolly et al. |
| 2003/0130616 A1 | 7/2003 | Steil et al. | 2004/0253736 A1 | 12/2004 | Stout et al. |
| 2003/0134347 A1 | 7/2003 | Heller et al. | 2004/0254429 A1 | 12/2004 | Yang |
| 2003/0135100 A1 | 7/2003 | Kim et al. | 2004/0254433 A1 | 12/2004 | Bandis et al. |
| 2003/0135333 A1 | 7/2003 | Aceti et al. | 2004/0254434 A1 | 12/2004 | Goodnow et al. |
| 2003/0153820 A1 | 8/2003 | Berner et al. | 2004/0260363 A1 | 12/2004 | Von Arx et al. |
| 2003/0153821 A1 | 8/2003 | Berner et al. | 2004/0263354 A1 | 12/2004 | Mann et al. |
| 2003/0158472 A1 | 8/2003 | Sohrab | 2005/0003470 A1 | 1/2005 | Nelson et al. |
| 2003/0158707 A1 | 8/2003 | Doi | 2005/0010087 A1 | 1/2005 | Banet et al. |
| 2003/0168338 A1 | 9/2003 | Gao et al. | 2005/0010269 A1 | 1/2005 | Lebel et al. |
| 2003/0175806 A1 | 9/2003 | Rule et al. | 2005/0027177 A1 | 2/2005 | Shin et al. |
| 2003/0176183 A1 | 9/2003 | Drucker et al. | 2005/0027179 A1 | 2/2005 | Berner et al. |
| 2003/0176933 A1 | 9/2003 | Lebel et al. | 2005/0027180 A1 | 2/2005 | Goode, Jr. et al. |
| 2003/0181851 A1 | 9/2003 | Mann et al. | 2005/0027181 A1 | 2/2005 | Goode, Jr. et al. |
| 2003/0181852 A1 | 9/2003 | Mann et al. | 2005/0027462 A1 | 2/2005 | Goode, Jr. et al. |
| 2003/0187338 A1 | 10/2003 | Say et al. | 2005/0027463 A1 | 2/2005 | Goode, Jr. et al. |
| 2003/0187525 A1 | 10/2003 | Mann et al. | 2005/0031689 A1 | 2/2005 | Shults et al. |
| 2003/0191376 A1 | 10/2003 | Samuels et al. | 2005/0033132 A1 | 2/2005 | Shults et al. |
| 2003/0191431 A1 | 10/2003 | Mann et al. | 2005/0038680 A1 | 2/2005 | McMahon |
| 2003/0195403 A1 | 10/2003 | Berner et al. | 2005/0043598 A1 | 2/2005 | Goode, Jr. et al. |
| 2003/0195462 A1 | 10/2003 | Mann et al. | 2005/0043894 A1 | 2/2005 | Fernandez |

| | | | | | | |
|---|---|---|---|---|---|---|
| 2005/0049473 A1 | 3/2005 | Desai et al. | | 2006/0036143 A1 | 2/2006 | Brister et al. |
| 2005/0051427 A1 | 3/2005 | Brauker et al. | | 2006/0036144 A1 | 2/2006 | Brister et al. |
| 2005/0051440 A1 | 3/2005 | Simpson et al. | | 2006/0036145 A1 | 2/2006 | Brister et al. |
| 2005/0054909 A1 | 3/2005 | Petisce et al. | | 2006/0036187 A1 | 2/2006 | Vos et al. |
| 2005/0056552 A1 | 3/2005 | Simpson et al. | | 2006/0040402 A1 | 2/2006 | Brauker et al. |
| 2005/0090607 A1 | 4/2005 | Tapsak et al. | | 2006/0052679 A1 | 3/2006 | Kotulla et al. |
| 2005/0112169 A1 | 5/2005 | Brauker et al. | | 2006/0058602 A1 | 3/2006 | Kwiatkowski et al. |
| 2005/0113657 A1 | 5/2005 | Alarcon et al. | | 2006/0063218 A1 | 3/2006 | Bartkowiak et al. |
| 2005/0113658 A1 | 5/2005 | Jacobson et al. | | 2006/0068208 A1 | 3/2006 | Tapsak et al. |
| 2005/0118726 A1 | 6/2005 | Schultz et al. | | 2006/0074564 A1 | 4/2006 | Bartkowiak et al. |
| 2005/0121322 A1 | 6/2005 | Say et al. | | 2006/0086624 A1 | 4/2006 | Tapsak et al. |
| 2005/0124873 A1 | 6/2005 | Shults et al. | | 2006/0155180 A1 | 7/2006 | Brister et al. |
| 2005/0131346 A1 | 6/2005 | Douglas | | 2006/0173444 A1 | 8/2006 | Choy et al. |
| 2005/0137471 A1 | 6/2005 | Haar et al. | | 2006/0183984 A1 | 8/2006 | Dobbles et al. |
| 2005/0143635 A1 | 6/2005 | Kamath et al. | | 2006/0183985 A1 | 8/2006 | Brister et al. |
| 2005/0143636 A1 | 6/2005 | Zhang et al. | | 2006/0189856 A1 | 8/2006 | Petisce et al. |
| 2005/0143675 A1 | 6/2005 | Neel et al. | | 2006/0189863 A1 | 8/2006 | Peyser et al. |
| 2005/0148003 A1 | 7/2005 | Keith et al. | | 2006/0195029 A1 | 8/2006 | Shults et al. |
| 2005/0154271 A1 | 7/2005 | Rasdal et al. | | 2006/0198864 A1 | 9/2006 | Shults et al. |
| 2005/0161346 A1 | 7/2005 | Simpson et al. | | 2006/0200019 A1 | 9/2006 | Petisce et al. |
| 2005/0171503 A1 | 8/2005 | Van Den Berghe et al. | | 2006/0200020 A1 | 9/2006 | Brister et al. |
| 2005/0171513 A1 | 8/2005 | Mann et al. | | 2006/0200022 A1 | 9/2006 | Brauker et al. |
| 2005/0173245 A1 | 8/2005 | Feldman et al. | | 2006/0211921 A1 | 9/2006 | Brauker et al. |
| 2005/0176136 A1 | 8/2005 | Burd et al. | | 2006/0222566 A1 | 10/2006 | Brauker et al. |
| 2005/0177036 A1 | 8/2005 | Shults et al. | | 2006/0224108 A1 | 10/2006 | Brauker et al. |
| 2005/0181012 A1 | 8/2005 | Saint et al. | | 2006/0235285 A1 | 10/2006 | Brister et al. |
| 2005/0182306 A1 | 8/2005 | Sloan | | 2006/0247985 A1 | 11/2006 | Liamos et al. |
| 2005/0182451 A1 | 8/2005 | Griffin et al. | | 2006/0258929 A1 | 11/2006 | Goode, Jr. et al. |
| 2005/0187720 A1 | 8/2005 | Goode, Jr. et al. | | 2006/0270922 A1 | 11/2006 | Brauker et al. |
| 2005/0192557 A1 | 9/2005 | Brauker et al. | | 2006/0270923 A1 | 11/2006 | Brauker et al. |
| 2005/0195930 A1 | 9/2005 | Spital et al. | | 2007/0016381 A1 | 1/2007 | Kamath et al. |
| 2005/0199494 A1 | 9/2005 | Say et al. | | 2007/0027381 A1 | 2/2007 | Stafford |
| 2005/0203360 A1 | 9/2005 | Brauker et al. | | 2007/0027384 A1 | 2/2007 | Brister et al. |
| 2005/0203707 A1 | 9/2005 | Tsutsui et al. | | 2007/0027385 A1 | 2/2007 | Brister et al. |
| 2005/0214892 A1 | 9/2005 | Kovatchev et al. | | 2007/0032706 A1 | 2/2007 | Kamath et al. |
| 2005/0215871 A1 | 9/2005 | Feldman et al. | | 2007/0032717 A1 | 2/2007 | Brister et al. |
| 2005/0215872 A1 | 9/2005 | Berner et al. | | 2007/0032718 A1 | 2/2007 | Shults et al. |
| 2005/0239154 A1 | 10/2005 | Feldman et al. | | 2007/0045902 A1 | 3/2007 | Brauker et al. |
| 2005/0239156 A1 | 10/2005 | Drucker et al. | | 2007/0060814 A1 | 3/2007 | Stafford |
| 2005/0245795 A1 | 11/2005 | Goode, Jr. et al. | | 2007/0066873 A1 | 3/2007 | Kamath et al. |
| 2005/0245799 A1 | 11/2005 | Brauker et al. | | 2007/0078320 A1 | 4/2007 | Stafford |
| 2005/0251083 A1 | 11/2005 | Carr-Brendel et al. | | 2007/0078321 A1 | 4/2007 | Mazza et al. |
| 2005/0261660 A1 | 11/2005 | Choi | | 2007/0093704 A1 | 4/2007 | Brister et al. |
| 2005/0267780 A1 | 12/2005 | Ray et al. | | 2007/0106135 A1 | 5/2007 | Sloan et al. |
| 2005/0271546 A1 | 12/2005 | Gerber et al. | | 2007/0149873 A1 | 6/2007 | Say et al. |
| 2005/0271547 A1 | 12/2005 | Gerber et al. | | 2007/0149874 A1 | 6/2007 | Say et al. |
| 2005/0272640 A1 | 12/2005 | Doyle, III et al. | | 2007/0151869 A1 | 7/2007 | Heller et al. |
| 2005/0272985 A1 | 12/2005 | Kotulla et al. | | 2007/0161879 A1 | 7/2007 | Say et al. |
| 2005/0277164 A1 | 12/2005 | Drucker et al. | | 2007/0161880 A1 | 7/2007 | Say et al. |
| 2005/0287620 A1 | 12/2005 | Heller et al. | | 2007/0163880 A1 | 7/2007 | Woo et al. |
| 2006/0001538 A1 | 1/2006 | Kraft et al. | | 2007/0179370 A1 | 8/2007 | Say et al. |
| 2006/0001550 A1 | 1/2006 | Mann et al. | | 2007/0179372 A1 | 8/2007 | Say et al. |
| 2006/0001551 A1 | 1/2006 | Kraft et al. | | 2007/0191699 A1 | 8/2007 | Say et al. |
| 2006/0003398 A1 | 1/2006 | Heller et al. | | 2007/0191700 A1 | 8/2007 | Say et al. |
| 2006/0004271 A1 | 1/2006 | Peyser et al. | | 2007/0197889 A1 | 8/2007 | Brister et al. |
| 2006/0007017 A1 | 1/2006 | Mann et al. | | 2007/0203408 A1 | 8/2007 | Say et al. |
| 2006/0015020 A1 | 1/2006 | Neale et al. | | 2007/0203410 A1 | 8/2007 | Say et al. |
| 2006/0015024 A1 | 1/2006 | Brister et al. | | 2007/0203411 A1 | 8/2007 | Say et al. |
| 2006/0016700 A1 | 1/2006 | Brister et al. | | 2007/0203966 A1 | 8/2007 | Brauker et al. |
| 2006/0019327 A1 | 1/2006 | Brister et al. | | 2007/0208244 A1 | 9/2007 | Brauker et al. |
| 2006/0020186 A1 | 1/2006 | Brister et al. | | 2007/0208245 A1 | 9/2007 | Brauker et al. |
| 2006/0020187 A1 | 1/2006 | Brister et al. | | 2007/0208246 A1 | 9/2007 | Brauker et al. |
| 2006/0020188 A1 | 1/2006 | Kamath et al. | | 2007/0208247 A1 | 9/2007 | Say et al. |
| 2006/0020189 A1 | 1/2006 | Brister et al. | | 2007/0213610 A1 | 9/2007 | Say et al. |
| 2006/0020190 A1 | 1/2006 | Kamath et al. | | 2007/0213611 A1 | 9/2007 | Simpson et al. |
| 2006/0020191 A1 | 1/2006 | Brister et al. | | 2007/0215491 A1 | 9/2007 | Heller et al. |
| 2006/0020192 A1 | 1/2006 | Brister et al. | | 2007/0218097 A1 | 9/2007 | Heller et al. |
| 2006/0025663 A1 | 2/2006 | Talbot et al. | | 2007/0235331 A1 | 10/2007 | Simpson et al. |
| 2006/0031094 A1 | 2/2006 | Cohen et al. | | 2007/0244380 A1 | 10/2007 | Say et al. |
| 2006/0036139 A1 | 2/2006 | Brister et al. | | 2007/0249919 A1 | 10/2007 | Say et al. |
| 2006/0036140 A1 | 2/2006 | Brister et al. | | 2007/0249920 A1 | 10/2007 | Say et al. |
| 2006/0036141 A1 | 2/2006 | Kamath et al. | | 2007/0249922 A1 | 10/2007 | Peyser et al. |
| 2006/0036142 A1 | 2/2006 | Brister et al. | | 2008/0021436 A1 | 1/2008 | Wolpert et al. |

| | | | | | |
|---|---|---|---|---|---|
| 2008/0021666 A1 | 1/2008 | Goode, Jr. et al. | 2009/0076361 A1 | 3/2009 | Kamath et al. |
| 2008/0033254 A1 | 2/2008 | Kamath et al. | 2009/0089999 A1 | 4/2009 | Say et al. |
| 2008/0033271 A1 | 2/2008 | Say et al. | 2009/0093696 A1 | 4/2009 | Say et al. |
| 2008/0045824 A1 | 2/2008 | Tapsak et al. | 2009/0099432 A1 | 4/2009 | Say et al. |
| 2008/0071156 A1 | 3/2008 | Brister et al. | 2009/0099435 A1 | 4/2009 | Say et al. |
| 2008/0076997 A1 | 3/2008 | Peyser et al. | 2009/0099436 A1 | 4/2009 | Brister et al. |
| 2008/0083617 A1 | 4/2008 | Simpson et al. | 2009/0124877 A1 | 5/2009 | Goode, Jr. et al. |
| 2008/0086039 A1 | 4/2008 | Heller et al. | 2009/0124878 A1 | 5/2009 | Goode, Jr. et al. |
| 2008/0086040 A1 | 4/2008 | Heller et al. | 2009/0124879 A1 | 5/2009 | Brister et al. |
| 2008/0086041 A1 | 4/2008 | Heller et al. | 2009/0124964 A1 | 5/2009 | Leach et al. |
| 2008/0086042 A1 | 4/2008 | Brister et al. | 2009/0131768 A1 | 5/2009 | Simpson et al. |
| 2008/0086043 A1 | 4/2008 | Heller et al. | 2009/0131769 A1 | 5/2009 | Leach et al. |
| 2008/0086044 A1 | 4/2008 | Brister et al. | 2009/0131776 A1 | 5/2009 | Simpson et al. |
| 2008/0086273 A1 | 4/2008 | Shults et al. | 2009/0131777 A1 | 5/2009 | Simpson et al. |
| 2008/0091094 A1 | 4/2008 | Heller et al. | 2009/0137886 A1 | 5/2009 | Shariati et al. |
| 2008/0091095 A1 | 4/2008 | Heller et al. | 2009/0137887 A1 | 5/2009 | Shariati et al. |
| 2008/0091096 A1 | 4/2008 | Say et al. | 2009/0143659 A1 | 6/2009 | Li et al. |
| 2008/0108942 A1 | 5/2008 | Brister et al. | 2009/0143660 A1 | 6/2009 | Brister et al. |
| 2008/0167543 A1 | 7/2008 | Say et al. | 2009/0156919 A1 | 6/2009 | Brister et al. |
| 2008/0183061 A1 | 7/2008 | Goode, Jr. et al. | 2009/0156924 A1 | 6/2009 | Shariati et al. |
| 2008/0183399 A1 | 7/2008 | Goode, Jr. et al. | 2009/0163781 A1 | 6/2009 | Say et al. |
| 2008/0188731 A1 | 8/2008 | Brister et al. | 2009/0163788 A1 | 6/2009 | Say et al. |
| 2008/0189051 A1 | 8/2008 | Goode, Jr. et al. | 2009/0163789 A1 | 6/2009 | Say et al. |
| 2008/0194935 A1 | 8/2008 | Brister et al. | 2009/0163790 A1 | 6/2009 | Brister et al. |
| 2008/0194936 A1 | 8/2008 | Goode, Jr. et al. | 2009/0163791 A1 | 6/2009 | Brister et al. |
| 2008/0194937 A1 | 8/2008 | Goode, Jr. et al. | 2009/0171179 A1 | 7/2009 | Say et al. |
| 2008/0194938 A1 | 8/2008 | Brister et al. | 2009/0173628 A1 | 7/2009 | Say et al. |
| 2008/0195232 A1 | 8/2008 | Carr-Brendel et al. | 2009/0177054 A1 | 7/2009 | Say et al. |
| 2008/0195967 A1 | 8/2008 | Goode, Jr. et al. | 2009/0177055 A1 | 7/2009 | Say et al. |
| 2008/0197024 A1 | 8/2008 | Simpson et al. | 2009/0177056 A1 | 7/2009 | Say et al. |
| 2008/0200788 A1 | 8/2008 | Brister et al. | 2009/0177057 A1 | 7/2009 | Say et al. |
| 2008/0200789 A1 | 8/2008 | Brister et al. | 2009/0177058 A1 | 7/2009 | Say et al. |
| 2008/0200791 A1 | 8/2008 | Simpson et al. | 2009/0177059 A1 | 7/2009 | Say et al. |
| 2008/0208025 A1 | 8/2008 | Shults et al. | 2009/0177060 A1 | 7/2009 | Say et al. |
| 2008/0214914 A1 | 9/2008 | Say et al. | 2009/0177061 A1 | 7/2009 | Say et al. |
| 2008/0214915 A1 | 9/2008 | Brister et al. | 2009/0177062 A1 | 7/2009 | Say et al. |
| 2008/0214918 A1 | 9/2008 | Brister et al. | 2009/0177063 A1 | 7/2009 | Say et al. |
| 2008/0228051 A1 | 9/2008 | Shults et al. | 2009/0177064 A1 | 7/2009 | Say et al. |
| 2008/0228054 A1 | 9/2008 | Shults et al. | 2009/0177065 A1 | 7/2009 | Say et al. |
| 2008/0242961 A1 | 10/2008 | Brister et al. | 2009/0177066 A1 | 7/2009 | Say et al. |
| 2008/0262329 A1 | 10/2008 | Say et al. | 2009/0178459 A1 | 7/2009 | Li et al. |
| 2008/0262469 A1 | 10/2008 | Brister et al. | 2009/0182212 A1 | 7/2009 | Say et al. |
| 2008/0269672 A1 | 10/2008 | Say et al. | 2009/0182213 A1 | 7/2009 | Say et al. |
| 2008/0275313 A1 | 11/2008 | Brister et al. | 2009/0182214 A1 | 7/2009 | Say et al. |
| 2008/0287764 A1 | 11/2008 | Rasdal et al. | 2009/0182215 A1 | 7/2009 | Say et al. |
| 2008/0287765 A1 | 11/2008 | Rasdal et al. | 2009/0182217 A1 | 7/2009 | Li et al. |
| 2008/0287766 A1 | 11/2008 | Rasdal et al. | 2009/0187088 A1 | 7/2009 | Say et al. |
| 2008/0296155 A1 | 12/2008 | Shults et al. | 2009/0187089 A1 | 7/2009 | Say et al. |
| 2008/0306368 A1 | 12/2008 | Goode, Jr. et al. | 2009/0187090 A1 | 7/2009 | Say et al. |
| 2008/0306434 A1 | 12/2008 | Dobbles et al. | 2009/0187091 A1 | 7/2009 | Say et al. |
| 2008/0306435 A1 | 12/2008 | Kamath et al. | 2009/0187092 A1 | 7/2009 | Say et al. |
| 2008/0306444 A1 | 12/2008 | Brister et al. | 2009/0187093 A1 | 7/2009 | Say et al. |
| 2008/0319292 A1 | 12/2008 | Say et al. | 2009/0187094 A1 | 7/2009 | Say et al. |
| 2009/0012379 A1 | 1/2009 | Goode, Jr. et al. | 2009/0187095 A1 | 7/2009 | Say et al. |
| 2009/0018424 A1 | 1/2009 | Kamath et al. | 2009/0192366 A1 | 7/2009 | Mensinger et al. |
| 2009/0030294 A1 | 1/2009 | Petisce et al. | 2009/0192368 A1 | 7/2009 | Say et al. |
| 2009/0036758 A1 | 2/2009 | Brauker et al. | 2009/0192369 A1 | 7/2009 | Say et al. |
| 2009/0036763 A1 | 2/2009 | Brauker et al. | 2009/0192370 A1 | 7/2009 | Say et al. |
| 2009/0043181 A1 | 2/2009 | Brauker et al. | 2009/0192371 A1 | 7/2009 | Say et al. |
| 2009/0043182 A1 | 2/2009 | Brauker et al. | 2009/0192372 A1 | 7/2009 | Say et al. |
| 2009/0043525 A1 | 2/2009 | Brauker et al. | 2009/0192373 A1 | 7/2009 | Say et al. |
| 2009/0043541 A1 | 2/2009 | Brauker et al. | 2009/0192374 A1 | 7/2009 | Say et al. |
| 2009/0043542 A1 | 2/2009 | Brauker et al. | 2009/0192375 A1 | 7/2009 | Say et al. |
| 2009/0045055 A1 | 2/2009 | Rhodes et al. | 2009/0192376 A1 | 7/2009 | Say et al. |
| 2009/0062633 A1 | 3/2009 | Brauker et al. | 2009/0192377 A1 | 7/2009 | Say et al. |
| 2009/0062634 A1 | 3/2009 | Say et al. | 2009/0192378 A1 | 7/2009 | Say et al. |
| 2009/0062635 A1 | 3/2009 | Brauker et al. | 2009/0192379 A1 | 7/2009 | Say et al. |
| 2009/0069655 A1 | 3/2009 | Say et al. | 2009/0192380 A1 | 7/2009 | Shariati et al. |
| 2009/0069656 A1 | 3/2009 | Say et al. | 2009/0192722 A1 | 7/2009 | Shariati et al. |
| 2009/0069657 A1 | 3/2009 | Say et al. | 2009/0192724 A1 | 7/2009 | Brauker et al. |
| 2009/0069658 A1 | 3/2009 | Say et al. | 2009/0192745 A1 | 7/2009 | Kamath et al. |
| 2009/0076356 A1 | 3/2009 | Simpson et al. | 2009/0192751 A1 | 7/2009 | Kamath et al. |
| 2009/0076360 A1 | 3/2009 | Brister et al. | 2009/0198115 A1 | 8/2009 | Say et al. |

| Publication No. | Date | Inventor |
|---|---|---|
| 2009/0198116 A1 | 8/2009 | Say et al. |
| 2009/0198175 A1 | 8/2009 | Say et al. |
| 2009/0203978 A1 | 8/2009 | Say et al. |
| 2009/0203981 A1 | 8/2009 | Brauker et al. |
| 2009/0204341 A1 | 8/2009 | Brauker et al. |
| 2009/0209838 A1 | 8/2009 | Say et al. |
| 2009/0216101 A1 | 8/2009 | Say et al. |
| 2009/0216103 A1 | 8/2009 | Brister et al. |
| 2009/0227940 A1 | 9/2009 | Say et al. |
| 2009/0227941 A1 | 9/2009 | Say et al. |
| 2009/0228214 A1 | 9/2009 | Say et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |

FOREIGN PATENT DOCUMENTS

| | | |
|---|---|---|
| DE | 227029 | 9/1985 |
| DE | 3934299 | 10/1990 |
| DE | 4234553 | 1/1995 |
| DE | 4401400 | 7/1995 |
| EP | 0010375 | 4/1980 |
| EP | 1579690 | 11/1980 |
| EP | 0026995 | 4/1981 |
| EP | 0048090 | 3/1982 |
| EP | 0078636 | 5/1983 |
| EP | 0096228 | 12/1983 |
| EP | 0096288 | 12/1983 |
| EP | 0098592 | 1/1984 |
| EP | 0125139 | 11/1984 |
| EP | 0127958 | 12/1984 |
| EP | 0136362 | 4/1985 |
| EP | 0170375 | 2/1986 |
| EP | 0177743 | 4/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0320109 | 6/1989 |
| EP | 0353328 | 2/1990 |
| EP | 0359831 | 3/1990 |
| EP | 0368209 | 5/1990 |
| EP | 0368290 | 5/1990 |
| EP | 0390390 | 10/1990 |
| EP | 0396788 | 11/1990 |
| EP | 0400918 | 12/1990 |
| EP | 0453283 | 10/1991 |
| EP | 0470290 | 2/1992 |
| EP | 0504835 | 9/1992 |
| EP | 0286118 | 1/1995 |
| EP | 0653718 | 5/1995 |
| EP | 0800082 | 10/1997 |
| EP | 0080304 | 6/1998 |
| EP | 0880936 | 12/1998 |
| EP | 0970655 | 1/2000 |
| EP | 1034734 | 9/2000 |
| EP | 1048264 | 11/2000 |
| GB | 1394171 | 5/1975 |
| GB | 1579690 | 11/1980 |
| GB | 1599241 | 9/1981 |
| GB | 2073891 | 10/1981 |
| GB | 2154003 | 8/1985 |
| GB | 2194892 | 3/1988 |
| GB | 2204408 | 11/1988 |
| GB | 2225637 | 6/1990 |
| GB | 2254436 | 10/1992 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 60-210243 | 10/1985 |
| JP | 61-090050 | 5/1986 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 1-114746 | 5/1989 |
| JP | 1-114747 | 5/1989 |
| JP | 1-124060 | 5/1989 |
| JP | 1-134244 | 5/1989 |
| JP | 1-156658 | 6/1989 |
| JP | 2-062958 | 3/1990 |
| JP | 2-120655 | 5/1990 |
| JP | 2-287145 | 11/1990 |
| JP | 2-310457 | 12/1990 |
| JP | 3-026956 | 2/1991 |
| JP | 3-028752 | 2/1991 |
| JP | 3-202764 | 9/1991 |
| JP | 5-072171 | 3/1993 |
| JP | 5-196595 | 8/1993 |
| JP | 6-190050 | 7/1994 |
| JP | 7-055757 | 3/1995 |
| JP | 7-072585 | 3/1995 |
| JP | 8-154903 | 6/1996 |
| JP | 8-285814 | 11/1996 |

| | | |
|---|---|---|
| JP | 8-285815 | 11/1996 |
| JP | 9-021778 | 1/1997 |
| JP | 9-101280 | 4/1997 |
| JP | 9-285459 | 11/1997 |
| JP | 10-170471 | 6/1999 |
| JP | 2000-000231 | 1/2000 |
| JP | 2000-116628 | 4/2000 |
| SU | 1281988 | 1/1987 |
| WO | WO-85/05119 | 11/1985 |
| WO | WO-86/00513 | 1/1986 |
| WO | WO-87/00513 | 1/1987 |
| WO | WO-87/06040 | 10/1987 |
| WO | WO-89/02246 | 3/1989 |
| WO | WO-89/05119 | 6/1989 |
| WO | WO-89/08713 | 9/1989 |
| WO | WO-90/00367 | 1/1990 |
| WO | WO-90/05300 | 5/1990 |
| WO | WO-90/05910 | 5/1990 |
| WO | WO-91/01680 | 2/1991 |
| WO | WO-91/04704 | 4/1991 |
| WO | WO-91/15993 | 10/1991 |
| WO | WO-92/13271 | 8/1992 |
| WO | WO-94/20602 | 9/1994 |
| WO | WO-94/27140 | 11/1994 |
| WO | WO-95/06240 | 3/1995 |
| WO | WO-96/07908 | 3/1996 |
| WO | WO-96/14026 | 5/1996 |
| WO | WO-96/25089 | 8/1996 |
| WO | WO-96/30431 | 10/1996 |
| WO | WO-96/35370 | 11/1996 |
| WO | WO-97/02847 | 1/1997 |
| WO | WO-97/19344 | 5/1997 |
| WO | WO-97/20207 | 6/1997 |
| WO | WO-97/41421 | 11/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-97/46868 | 12/1997 |
| WO | WO-98/09167 | 3/1998 |
| WO | WO-98/24366 | 6/1998 |
| WO | WO-98/52045 | 11/1998 |
| WO | WO-98/52293 | 11/1998 |
| WO | WO-98/56293 | 12/1998 |
| WO | WO-99/05966 | 2/1999 |
| WO | WO-99/13574 | 3/1999 |
| WO | WO-99/32883 | 7/1999 |
| WO | WO-99/56613 | 11/1999 |
| WO | WO-99/58973 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/33065 | 6/2000 |
| WO | WO-00/49940 | 8/2000 |
| WO | WO-00/59370 | 10/2000 |
| WO | WO-00/62664 | 10/2000 |
| WO | WO-00/62665 | 10/2000 |
| WO | WO-00/74753 | 12/2000 |
| WO | WO-00/78210 | 12/2000 |
| WO | WO 00/78992 | 12/2000 |
| WO | WO-01/24038 | 4/2001 |
| WO | WO-01/33216 | 5/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/58348 | 8/2001 |
| WO | WO-01/67009 | 9/2001 |
| WO | WO-01/68901 | 9/2001 |
| WO | WO 02/16905 A2 | 2/2002 |
| WO | WO-02/17210 | 2/2002 |
| WO | WO-02/58537 | 8/2002 |
| WO | WO-02/058537 | 8/2002 |
| WO | WO-02/078512 | 10/2002 |
| WO | WO 03/076893 A2 | 9/2003 |
| WO | WO 03/0820191 A2 | 10/2003 |
| WO | WO 2004/061420 A2 | 7/2004 |
| WO | WO 2004/061420 A3 | 7/2004 |
| WO | WO 2005/089103 A2 | 9/2005 |
| WO | WO-2006-119084 | 11/2006 |
| WO | WO-2006/119084 | 11/2006 |
| WO | WO-2007/002189 | 1/2007 |
| WO | WO-2007/016399 | 2/2007 |
| WO | WO-2007-016399 | 2/2007 |
| WO | WO-2007/027381 | 3/2007 |
| WO | WO-2007-027381 | 3/2007 |
| WO | WO-2007/027788 | 3/2007 |
| WO | WO-2007/051139 | 5/2007 |
| WO | WO-2007/053832 | 5/2007 |
| WO | WO-2007/056638 | 5/2007 |
| WO | WO-2007/120363 | 10/2007 |

OTHER PUBLICATIONS

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of The Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry* vol. 10, 1965, pp. 295-305.

Armour, J. C., et al., "Application of Chronic Intravascular Blood Glucose Sensor in Dogs", *Diabetes*, vol. 39, 1990, pp. 1519-1526.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Boedeker Plastics, Inc., "Polyethylene Specifications", Web Page of Boedeker.com, 2007, pp. 1-3.

Brandt, J., et al., "Covalent Attachment of Proteins to Polysaccharide Carriers by Means of Benzoquinone", *Biochimica et Biophysica Acta*, vol. 386, 1975, pp. 196-202.

Brooks, S. L., et al., "Development of an On-Line Glucose Sensor for Fermentation Monitoring", *Biosensors*, vol. 3, 1987/88, pp. 45-56.

Brownlee, M., et al., "A Glucose-Controlled Insulin-Delivery System: Semisynthetic Insulin Bound to Lectin", *Science*, vol. 206, 1979, 1190-1191.

Cass, A. E., et al., "Ferricinum Ion As An Electron Acceptor for Oxido-Reductases", *Journal of ElectroAnalytical Chemistry*, vol. 190, 1985, pp. 117-127.

Cass, A. E., et al., "Ferrocene-Mediated Enzyme Electrode for Amperometric Determination of Glucose", *Analytical Chemistry*, vol. 56, No. 4, 1984, 667-671.

Castner, J. F., et al., "Mass Transport and Reaction Kinetic Parameters Determined Electrochemically for Immobilized Glucose Oxidase", *Biochemistry*, vol. 23, No. 10, 1984, 2203-2210.

Claremont, D. J., et al., "Biosensors for Continuous in Vivo Glucose Monitoring", • *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Complaint, "*Abbott Diabetes Care, Inc. v. Dexcom, Inc.*", filed Aug. 11, 2005.

Complaint, Amended, "*Abbott Diabetes Care, Inc. v. Dexcom, Inc.*", filed Jun. 27, 2006.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.

Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.

Davis, G., "Electrochemical Techniques for the Development of Amperometric Biosensors", *Biosensors*, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al., "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of The Royal Society of London*, vol. 316, 1987, pp. 95-106.

Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Graham, N. B., "Poly(ethylene oxide) and Related Hydrogels," *Hydrogels in Medicine and Pharmacy*, vol. II: Polymers, Chapter 4, 1987, pp. 95-113.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Hamilton, "Hamilton Needle Gauge Index", www.hamiltoncompany.com.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*. vol. 60. No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts of Chemical Research* vol. 23, No. 5, 1990, 128-134.

Heller, A., et al., "Amperometric Biosensors Based on Three-Dimensional Hydrogel-Forming Epoxy Networks", *Sensors and Actuators B*, vol. 13-14, 1993, pp. 180-183.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al., "Immobilized Enzyme Chemically Modified Electrode as an Amperometric Sensor", *Analytical Chemistry*, vol. 53. No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49. No. 2, 1985, pp. 541-543.

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135, No. 1, 1988, pp. 112-115.

Kaplan, S. M., "Wiley Electrical and Electronics Engineering Dictionary", *IEEE Press*, 2004, pp. 141, 142, 548, 549.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-$\alpha$-Glycerophosphate L-Lactate Electrodes Based on the Electrochemical 'Wiring' of Oxidases", *Analytical Chemistry*, vol. 64, No. 9, 1992, pp. 1008-1013.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with $[Os(4,4'-dimethoxy-2,2'-bipyridine)_2Cl]^{+/2+}$", *Journal of the Chemical Society, Faraday Transactions*, vol. 92, No. 20, 1996, pp. 4131-4136.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koudelka, M., et al., "In-Vivo Behaviour of Hypodermically Implanted Microfabricated Glucose Sensors", *Biosensors & Bioelectronics*. vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research* vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Maidan, R., et al., "Elimination of Electrooxidizable Interferant-Produced Currents in Amperometric Biosensors", *Analytical Chemistry*, vol. 64, No. 23, 1992, pp. 2889-2896.

Marko-Varga, G., et al., "Enzyme-Based Biosensor as a Selective Detection Unit in Column Liquid Chromatography", *Journal of Chromatography A*, vol. 660, 1994, pp. 153-167.

Mastrototaro, J. J., et al., "An Electroenzymatic Glucose Sensor Fabricated on a Flexible Substrate", *Sensors and Actuators B*, vol. 5, 1991, pp. 139-144.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating In Vitro and In Vivo Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats", *Diabetologia*, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta.*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked $[Os(bpy)_2Cl]^{+/2+}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for In Vivo Use", *Tibtech*, vol. 11, 1993, pp. 285-291.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and In Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Reusch, W., "Other Topics: Organometallic Chemistry: Organometallic Compounds: Main Group Organometallic Compounds," *Virtual Textbook of Organic Chemistry*, 1999, Rev. 2007, 25 pages.

Sacks (ED), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*. vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F. W., et al., "Second Generation Biosensors," *Biosensors & Bioelectronics*, vol. 6, 1991, pp. 245-253.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of Analytical Data," *Fundamentals of Analytical Chemistry*, 1966, pp. 55.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M., "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol. 10, 1985, pp. 231-295.

Tatsuma, T., et al., "Enzyme Monolayer—and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)Cl]$^{+/2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27 No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for In Vivo Electrochemistry", *Analytical Letters*, vol. 24, No. 6, 1991, pp. 935-945.

U.S. Appl. No. 90/007,903, Request for Reexamination of U.S. Patent No. 6,565,509, filed Jan. 25, 2006.

U.S. Appl. No. 90/007,910, Request for Reexamination of U.S. Patent No. 6,175,752, filed Feb. 1, 2006.

U.S. Appl. No. 90/007,913, Request for Reexamination of U.S. Patent No. 6,284,478, filed Feb. 1, 2006.

U.S. Appl. No. 90/007,914, Request for Reexamination of U.S. Patent No. 6,329,161, filed Feb. 1, 2006.

U.S. Appl. No. 90/008,172, Request for Reexamination of U.S. Patent No. 6,990,366, filed Aug. 16, 2006.

U.S. Appl. No. 90/008,173, Request for Reexamination of U.S. Patent No. 6,134,461, filed Aug. 16, 2006.

U.S. Appl. No. 90/008,457, Request for Reexamination of U.S. Patent No. 6,990,366, filed Jan. 23, 2007.
U.S. Appl. No. 90/008,665, Request for Reexamination of U.S. Patent No. 6,284,478, filed May 25, 2007.
U.S. Appl. No. 90/008,713, Request for Reexamination of U.S. Patent No. 6,329,161, filed Jul. 25, 2007.
Umana, M., "Protein-Modified Electrochemically Active Biomaterial Surface", *U.S. Army Research Office, Analytical and Chemical Sciences Research Triangle Institute*, 1988, pp. 1-9.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Urban, G., et al., "Miniaturized Thin-Film Biosensors Using Covalently Immobilized Glucose Oxidase", *Biosensors & Bioelectronics*, vol. 6, 1991, pp. 555-562.
Velho, G., et al., "In Vitro and In Vivo Stability of Electrode Potentials in Needle-Type Glucose Sensors", *Diabetes*, vol. 38, No. 2, 1989, pp. 164-171.
Velho, G., et al., "Strategies for Calibrating a Subcutaneous Glucose Sensor", *Biomedica Biochimica Acta*, vol. 48, 1989, pp. 957-964.
Von Woedtke, T., et al., "In Situ Calibration of Implanted Electrochemical Glucose Sensors", *Biomedica Biochimica Acta*, vol. 48, 1989, pp. 943-952.
Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.
Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.
Wang, D. L., et al., "Miniaturized Flexible Amperometric Lactate Probe", *Analytical Chemistry*, vol. 65, No. 8, 1993, pp. 1069-1073.
Wang, J., et al., "Activation of Glassy Carbon Electrodes by Alternating Current Electrochemical Treatment", *Analytica Chimica Acta*, vol. 167, 1985, pp. 325-334.
Wang, J., et al., "Amperometric Biosensing of Organic Peroxides with Peroxidase-Modified Electrodes", *Analytica Chimica Acta*, vol. 254, 1991, pp. 81-88.
Wang, J., et al., "Screen-Printable Sol-Gel Enzyme-Containing Carbon Inks", *Analytical Chemistry*, vol. 68, No. 15, 1996, pp. 2705-2708.
Wang, J., et al., "Sol-Gel-Derived Metal-Dispersed Carbon Composite Amperometric Biosensors", *Electroanalysis*, vol. 9, No. 1, 1997, pp. 52-55.
Williams, D. L., et al., "Electrochemical-Enzymatic Analysis of Blood Glucose and Lactate", *Analytical Chemistry*, vol. 42, No. 1, 1970, pp. 118-121.
Wilson, G. S., et al., "Progress Toward the Development of an Implantable Sensor for Glucose", *Clinical Chemistry*, vol. 38, No. 9, 1992, pp. 1613-1617.
Yabuki, S., et al., "Electro-Conductive Enzyme Membrane", *Journal of the Chemical Society, Chemical Communications*, 1989, pp. 945-946.
Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.
Yang, L., et al., "Determination of Oxidase Enzyme Substrates Using Cross-Flow Thin-Layer Amperometry", *Electroanalysis*, vol. 8, No. 8-9, 1996, pp. 716-721.
Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.
Yao, T., "A Chemically-Modified Enzyme Membrane Electrode as an Amperometric Glucose Sensor", *Analytica Chimica Acta*, vol. 148, 1983, pp. 27-33.
Ye, L., et al., "High Current Density 'Wired' Quinoprotein Glucose Dehydrogenase Electrode", *Analytical Chemistry*, vol. 65, No. 3, 1993, pp. 238-241.
Yildiz, A., et al., "Evaluation of an Improved Thin-Layer Electrode", *Analytical Chemistry*, vol. 40, No. 7, 1968, pp. 1018-1024.
Zamzow, K., et al., "New Wearable Continuous Blood Glucose Monitor (BGM) and Artificial Pancreas (AP)", *Diabetes*, vol. 39, 1990, pp. 5A-20.
Zhang, Y., et al., "Application of Cell Culture Toxicity Tests to the Development of Implantable Biosensors", *Biosensors & Bioelectronics*, vol. 6, 1991, pp. 653-661.
Zhang, Y., et al., "Elimination of the Acetaminophen Interference in an Implantable Glucose Sensor", *Analytical Chemistry*, vol. 66, No. 7, 1994, pp. 1183-1188.
Supplementary European Search Report for Eurpoean Patent No. EP 03 80 8614 with International Filing Date of Dec. 26, 2003.
Blank, T., et al., "Clinical Results from a Non-Invasive Blood Glucose Monitor," 2002; *Proceedings of SPIE*, vol. 4624.
Malin, S., et al., "Noninvasive Prediction of Glucose by Near-Infrared Diffuse Reflectance Spectroscopy," 1999, *Clinical Chemistry*, vol. 45, No. 9, pp. 1651-1658.
Feldman et al., "A Continuous Glucose Sensor Based on Wired Enzyme™ Technology—Results from a e-Day Trial in Patients with Type 1 Diabetes," *Diabetes Technology & Therapeutics*, vol. 5, No. 5, 2003, pp. 769-779.
McGarraugh et al., "Physiological Influences on Off-Finger Glucose Testing," *Diabetes Technology & Therapeutics*, vol. 3, No. 3, 2001, pp. 367-376.
Schmidtke et al., "Measurement and Modeling of the Transient Difference Between Blood and Subcutaneous Glucose Concentrations in the Rat after Injection of Insulin," *Proc. Natl. Acad. Sci. USA*, 95, 1998, pp. 294-299.
Csoregi, et al., "Design and Optimization of a Selectrive Subcutaneously Implantable Glucose Electrode Based on 'Wired' Glucose Oxidase," *Analytical Chemistry*, vol. 67, No. 7, Apr. 1, 1995.
McGarraugh et al., "Glucose Measurements Using Blood Extracted from the Forearm and the Finger," TheraSense, Inc., Alameda, CA, 2001, 16 pages.
Quinn, et al., "Kinetics of Glucose Delivery to Subcutaneous Tissue in Rats Measured with 0.3mm Amperometric Microsensors," *Am. J. Physiol.*, 269 (Endocrinol Metab. 32), 1995, pp. E155-E161.
Jungheim, et al., "Risk Delay of Hypoglycemia Detection by Glucose Monitoring at the Arm," *Diabetes Care*, vol. 24(7), Jul. 2001, pp. 1303-1304.
Bennion, et al., "Alternate Site Glucose Testing: A Crossover Design," *Diabetes Technology & Therapeutics*, vol. 4, No. 1, 2002, pp. 25-33.
Johnson, "Peripheral Circulation," *John Wiley & Sons*, 1978, p. 198.
Roe et al., "Bloodless Glucose Measurements," *Critical Reviews ™ in Therapeutic Drug Carrier Systems*, 15(3), 1998, pp. 199-241.
Jungheim et al., "How Rapid Does Glucose Concentration Change in Daily Life of Patients with Type 1 Diabetes?" Abstract, *Presented at the Second Annual Diabetes Technology Meeting, Diabetes Technology Society*, Atlanta, Georgia, Nov. 2002, p. 250.
John Lortz and Susan Leavitt, "What is Bluetooth? We Explain The Newest Short-Range Connectivity Technology," 2002, Sandhill Publishing, Smart Computing Learning Series Wireless Computing, pp. 72-74.
Feldman et al., "Correlation of Glucose Concentrations in Interstitial Fluid and Venous Blood During Periods of Rapid Glucose Change," *39th Annual Meeting of the German Diabetes Associates*, Hanover, Germany, May 19-22, 2004.
"PCT Notification of Transmittal of the International Search Report and the Written Opinion of the International Searching Authority, or the Declaration" for PCT Application No. PCT/US05/04892, filed Feb. 16, 2005.

\* cited by examiner

| Byte | High Nibble | Low Nibble |
|---|---|---|
| 0 | TX ID (lsbyte) | |
| 1 | Tx Time | |
| 2 | Tx Status | Tx Status n0 |
| 3 | Sensor n0 | Tx Status n2 |
| 4 | Sensor n2 | Sensor n1 |
| 5 | Tx Status-1 n1 | Tx Status-1 n0 |
| 6 | Sensor-1 n0 | Tx Status-1 n2 |
| 7 | Sensor-1 n2 | Sensor-1 n1 |
| 8 | Tx Status-2 n1 | Tx Status-2 n0 |
| 9 | Sensor-2 n0 | Tx Status-2 n2 |
| 10 | Sensor-2 n2 | Sensor-2 n1 |
| 11 | CV-1, Tx Status-1 | CV, Tx Status |
| 12 | Tx Pending, Tx Batt | CV-2, Tx Status-2 |

FIGURE 4

| 1 | Packed Data | 13 bytes |
|---|---|---|
| 2 | Tx ID, middle sb | 1 byte |
| 3 | Tx ID, msb | 1 byte |
| 4 | Zero Pad | 232 bytes |
| 5 | Parity Symbols | 8 bytes |
|   | Total | 255 bytes |

FIGURE 5A

| 1 | Packed data | 13 bytes |
|---|---|---|
| 2 | Parity Symbols | 8 bytes |
|   | Total | 21 bytes |

FIGURE 5B

| 1 | 0x00 0x00 0x12 0x34 | 4 bytes |
|---|---|---|
| 1 | Depadded Data Block Contents | 21 bytes |

FIGURE 5C

CONTINUOUS GLUCOSE MONITORING SYSTEM AND METHODS OF USE

RELATED APPLICATION

This application claims priority under 35 USC §119 to Provisional Patent Application No. 60/437,374 filed on Dec. 31, 2002, entitled "Continuous Glucose Monitoring System and Methods of Use", the disclosure of which is incorporated herein by reference for all purposes.

BACKGROUND

The present invention relates to continuous glucose monitoring systems. More specifically, the present invention relates to an in-vivo continuous glucose monitoring system which detects glucose levels continuously and transfers the detected glucose level information at predetermined time intervals to data processing devices for monitoring, diagnosis and analysis.

SUMMARY OF THE INVENTION

A continuous glucose monitoring system in accordance with one embodiment of the present invention includes a sensor configured to detect one or more glucose levels, a transmitter operatively coupled to the sensor, the transmitter configured to receive the detected one or more glucose levels, the transmitter further configured to transmit signals corresponding to the detected one or more glucose levels, a receiver operatively coupled to the transmitter configured to receive transmitted signals corresponding to the detected one or more glucose levels, where the transmitter is configured to transmit a current data point and at least one previous data point, the current data point and the at least one previous data point corresponding to the detected one or more glucose levels.

The receiver may be operatively coupled to the transmitter via an RF communication link, and further, configured to decode the encoded signals received from the transmitter.

In one embodiment, the transmitter may be configured to periodically transmit a detected and processed glucose level from the sensor to the receiver via the RF data communication link. In one embodiment, the transmitter may be configured to sample four times every second to obtain 240 data points for each minute, and to transmit at a rate of one data point (e.g., an average value of the 240 sampled data points for the minute) per minute to the receiver.

The transmitter may be alternately configured to transmit three data points per minute to the receiver, the first data point representing the current sampled data, and the remaining two transmitted data points representing the immediately past two data points previously sent to the receiver. In this manner, in the case where the receiver does not successfully receive the sampled data from the transmitter, at the subsequent data transmission, the immediately prior transmitted data is received by the receiver. Thus, even with a faulty connection between the transmitter and the receiver, or a failed RF data link, the present approach ensures that missed data points may be ascertained from the subsequent data point transmissions without retransmission of the missed data points to the receiver.

The transmitter may be configured to encode the detected one or more glucose levels received from the sensor to generate encoded signals, and to transmit the encoded signals to the receiver. In one embodiment, the transmitter may be configured to transmit the encoded signals to the receiver at a transmission rate of one data point per minute. Further, the transmitter may be configured to transmit the current data point and the at least one previous data points in a single transmission per minute to the receiver. In one aspect, the current data point may correspond to a current glucose level, and where the at least one previous data point may include at least two previous data points corresponding respectively to at least two consecutive glucose levels, the one of the at least two consecutive glucose levels immediately preceding the current glucose level.

In a further embodiment, the receiver may include an output unit for outputting the received transmitted signals corresponding to one or more glucose levels. The output unit may include a display unit for displaying data corresponding to the one or more glucose levels, where the display unit may include one of a LCD display, a cathode ray tube display, and a plasma display.

The displayed data may include one or more of an alphanumeric representation corresponding to the one or more glucose levels, a graphical representation of the one or more glucose levels, and a three-dimensional representation of the one or more glucose levels. Moreover, the display unit may be configured to display the data corresponding to the one or more glucose levels substantially in real time.

Further, the output unit may include a speaker for outputting an audio signal corresponding to the one or more glucose levels.

In yet a further embodiment, the receiver may be configured to store an identification information corresponding to the transmitter.

The receiver may be further configured to perform a time hopping procedure for synchronizing with the transmitter. Alternatively, the receiver may be configured to synchronize with the transmitter based on the signal strength detected from the transmitter, where the detected signal strength exceeds a preset threshold level.

The transmitter in one embodiment may be encased in a substantially water-tight housing to ensure continuous operation even in the situation where the transmitter is in contact with water.

Furthermore, the transmitter may be configured with a disable switch which allows the user to temporarily disable the transmission of data to the receiver when the user is required to disable electronic devices, for example, when aboard an airplane. In another embodiment, the transmitter may be configured to operate in an additional third state (such as under Class B radiated emissions standard) in addition to the operational state and the disable state discussed above, so as to allow limited operation while aboard an airplane yet still complying with the Federal Aviation Administration (FAA) regulations. Additionally, the disable switch may also be configured to switch the transmitter between various operating modes such as fully functional transmission mode, post-manufacture sleep mode, and so on. In this manner, the power supply for the transmitter is optimized for prolonged usage by effectively managing the power usage.

Furthermore, the transmitter may be configured to transmit the data to the receiver in predetermined data packets, encoded, in one embodiment, using Reed Solomon encoding, and transmitted via the RF communication link. Additionally, in a further aspect of the present invention, the RF communication link between the transmitter and the receiver of the continuous glucose monitoring system may be implemented using a low cost, off the shelf remote keyless entry (RKE) chip set.

The receiver in an additional embodiment may be configured to perform, among others, data decoding, error detection and correction (using, for example, forward error correction) on the encoded data packets received from the transmitter to minimize transmission errors such as transmitter stabilization errors and preamble bit errors resulting from noise. The receiver is further configured to perform a synchronized time hopping procedure with the transmitter to identify and synchronize with the corresponding transmitter for data transmission.

Additionally, the receiver may include a graphical user interface (GUI) for displaying the data received from the transmitter for the user. The GUI may include a liquid crystal display (LCD) with backlighting feature to enable visual display in dark surroundings. The receiver may also include an output unit for generating and outputting audible signal alerts for the user, or placing the receiver in a vibration mode for alerting the user by vibrating the receiver.

More specifically, in a further aspect, the receiver may be configured to, among others, display the received glucose levels on a display section of the receiver either real time or in response to user request, and provide visual (and/or auditory) notification to the user of the detected glucose levels being monitored. To this end, the receiver is configured to identify the corresponding transmitter from which it is to receive data via the RF data link, by initially storing the identification information of the transmitter, and performing a time hopping procedure to isolate the data transmission from the transmitter corresponding to the stored identification information and thus to synchronize with the transmitter. Alternatively, the receiver may be configured to identify the corresponding transmitter based on the signal strength detected from the transmitter, determined to exceed a preset threshold level.

A method in accordance with one embodiment of the present invention includes the steps of receiving an identification information corresponding to a transmitter, detecting data within a predetermined RF transmission range, determining whether the detected data is transmitted from the transmitter, decoding the detected data, and generating an output signal corresponding to the decoded data.

In one embodiment, the step of determining whether the detected data transmission is transmitted from the transmitter may be based on the received identification information. In another embodiment, the step of determining whether the detected data transmission is transmitted from the transmitter may be based on the signal strength and duration of the detected data within the predetermined RF transmission range.

In a further embodiment, the step of decoding may also include the step of performing error correction on the decoded data. Moreover, the step of decoding may include the step of performing Reed-Solomon decoding on the detected data.

In the manner described, the present invention provides a continuous glucose monitoring system that is simple to use and substantially compact so as to minimize any interference with the user's daily activities. Furthermore, the continuous glucose monitoring system may be configured to be substantially water-resistant so that the user may freely bathe, swim, or enjoy other water related activities while using the monitoring system. Moreover, the components comprising the monitoring system including the transmitter and the receiver are configured to operate in various modes to enable power savings, and thus enhancing post-manufacture shelf life.

INCORPORATION BY REFERENCE

Applicants herein incorporate by reference application Ser. No. 09/753,746 filed on Jan. 2, 2001, and issued on May 6, 2003 as U.S. Pat. No. 6,560,471, entitled "Analyte Monitoring Device and Methods of Use" assigned to the Assignee of the present application for all purposes.

BRIEF DESCRIPTION OF THE DRAWINGS

FIG. 4 illustrates a data packet of the transmitter of the continuous glucose monitoring system shown in FIG. 1 in accordance with one embodiment of the present invention;

FIGS. 5A, 5B, and 5C illustrate a data packet table for Reed-Solomon encoding in the transmitter, a depadded data table, and a link prefix table, respectively, in accordance with one embodiment of the continuous glucose monitoring system of FIG. 1.

DETAILED DESCRIPTION

Figure 1:
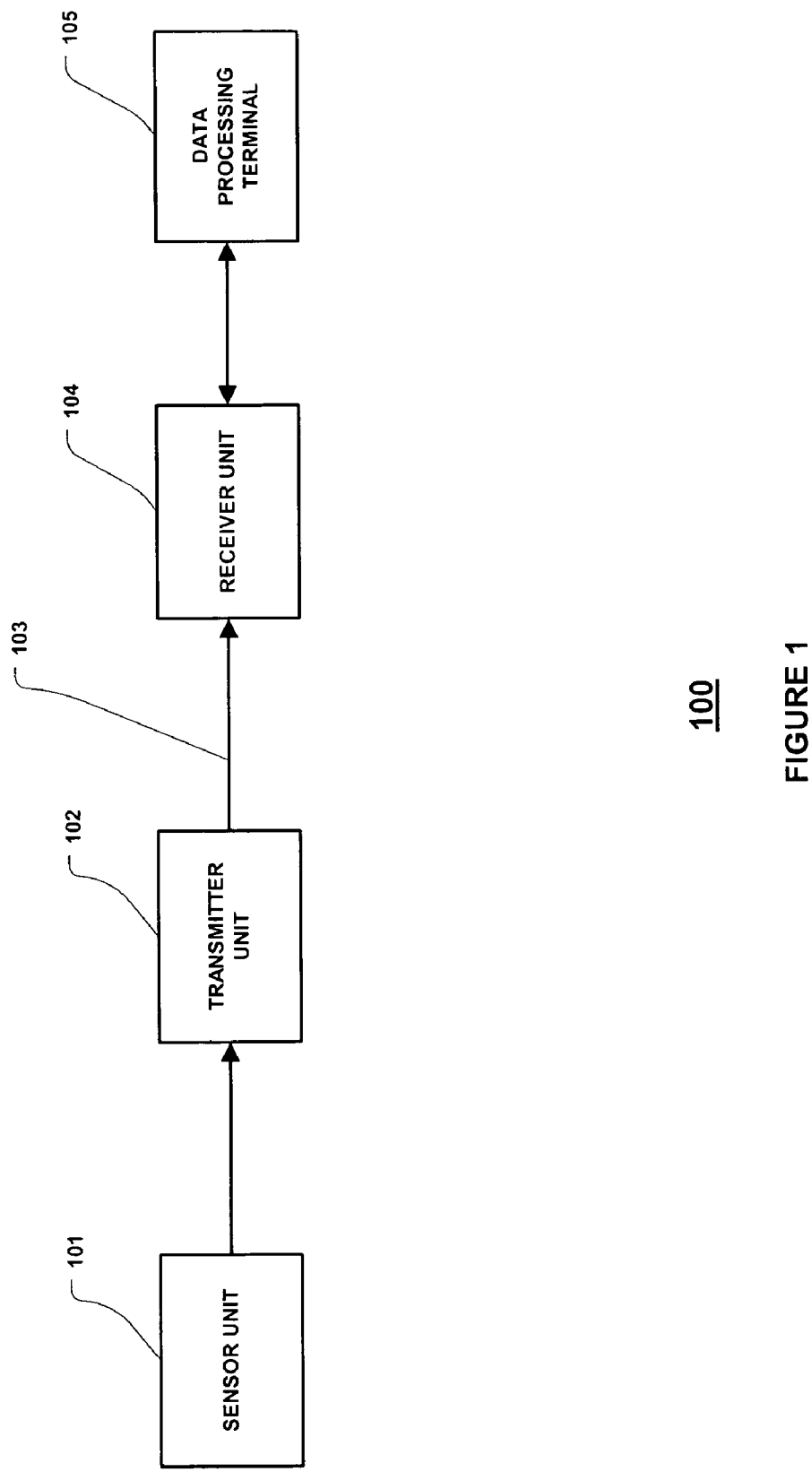
FIG. 1 illustrates a continuous glucose monitoring system in accordance with one embodiment of the present invention.

FIG. 1 illustrates a continuous glucose monitoring system 100 in accordance with one embodiment of the present invention. In such embodiment, the continuous glucose monitoring system 100 includes a sensor 101, a transmitter 102 coupled to the sensor 101, and a receiver 104 which is configured to communicate with the transmitter 102 via a communication link 103. The receiver 104 may be further configured to transmit data to a data processing terminal 105 for evaluating the data received by the receiver 104. Only one sensor 101, transmitter 102, communication link 103, receiver 104, and data processing terminal 105 are shown in the embodiment of the continuous glucose monitoring system 100 illustrated in FIG. 1. However, it will be appreciated by one of ordinary skill in the art that the continuous glucose monitoring system 100 may include one or more sensor 101, transmitter 102, communication link 103, receiver 104, and data processing terminal 105, where each receiver 104 is uniquely synchronized with a respective transmitter 102.

In one embodiment of the present invention, the sensor 101 is physically positioned on the body of a user whose glucose is being monitored. The term user as used herein is intended to include humans, animals, as well as any other who might benefit from the use of the glucose monitoring system 100. The sensor 101 is configured to continuously sample the glucose level of the user and convert the sampled glucose level into a corresponding data signal for transmission by the transmitter 102. In one embodiment, the transmitter 102 is mounted on the sensor 101 so that both devices are positioned on the user's body. The transmitter 102 performs data processing such as filtering and encoding on data signals, each of which corresponds to a sampled glucose level of the user, for transmission to the receiver 104 via the communication link 103.

In one embodiment, the continuous glucose monitoring system 100 is configured as a one-way RF communication path from the transmitter 102 to the receiver 104. In such embodiment, the transmitter 102 transmits the sampled data signals received from the sensor 101 without acknowledgement from the receiver 104 that the transmitted sampled data signals have been received. For example, the transmitter 102 may be configured to transmit the encoded sampled data signals at a fixed rate (e.g., at one minute intervals) after the completion of the initial power on procedure. Likewise, the receiver 104 may be configured to detect such transmitted encoded sampled data signals at predetermined time intervals.

As discussed in further detail below, in one embodiment of the present invention the receiver 104 includes two sections. The first section is an analog interface section that is configured to communicate with the transmitter 102 via the communication link 103. In one embodiment, the analog interface section may include an RF receiver and an antenna for receiving and amplifying the data signals from the transmitter 102, which are thereafter, demodulated with a local oscillator and filtered through a band-pass filter. The second section of the receiver 104 is a data processing section which is configured to process the data signals received from the transmitter 102 such as by performing data decoding, error detection and correction, data clock generation, and data bit recovery.

In operation, upon completing the power-on procedure, the receiver 104 is configured to detect the presence of the transmitter 102 within its range based on the strength of the detected data signals received from the transmitter 102. For example, in one embodiment, the receiver 104 is configured to detect signals whose strength exceeds a predetermined level to identify the transmitter 102 from which the receiver 104 is to receive data. Alternatively, the receiver 104 in a further embodiment may be configured to respond to signal transmission for a predetermined transmitter identification information of a particular transmitter 102 such that, rather than detecting the signal strength of a transmitter 102 to identify the transmitter, the receiver 104 may be configured to detect transmitted signal of a predetermined transmitter 102 based on the transmitted transmitter identification information corresponding to the pre-assigned transmitter identification information for the particular receiver 104.

In one embodiment, the identification information of the transmitters 102 includes a 16-bit ID number. In an alternate embodiment, the ID number may be a predetermined length including a 24-bit ID number or a 32-bit ID number. Further, any other length ID number may also be used. Thus, in the presence of multiple transmitters 102, the receiver 104 will only recognize the transmitter 102 which corresponds to the stored identification information. Data signals transmitted from the other transmitters within the range of the receiver 104 are considered invalid signals.

Referring again to FIG. 1, where the receiver 104 determines the corresponding transmitter 102 based on the signal strength of the transmitter 102, when the receiver 104 is initially powered-on, the receiver 104 is configured to continuously sample the signal strength of the data signals received from the transmitters within its range. If the signal strength of the data signals meets or exceeds the signal strength threshold level and the transmission duration threshold level, the receiver 104 returns a positive indication for the transmitter 102 transmitting the data signals. That is, in one embodiment, the receiver 104 is configured to positively identify the transmitter 102 after one data signal transmission. Thereafter, the receiver 104 is configured to detect positive indications for three consecutive data signals transmissions for a predetermined time period. At such point, after three consecutive transmissions, the transmitter 102 is fully synchronized with the receiver 104.

Upon identifying the appropriate transmitter 102, the receiver 104 begins a decoding procedure to decode the received data signals. In one embodiment, a sampling clock signal may be obtained from the preamble portion of the received data signals. The decoded data signals, which include fixed length data fields, are then sampled with the sampling clock signal. In one embodiment of the present invention, based on the received data signals and the time interval between each of the three data signal transmissions, the receiver 104 determines the wait time period for receiving the next transmission from the identified and synchronized transmitter 102. Upon successful synchronization, the receiver 104 begins receiving from the transmitter 102 data signals corresponding to the user's detected glucose level. As described in further detail below, the receiver 104 in one embodiment is configured to perform synchronized time hopping with the corresponding synchronized transmitter 102 via the communication link 103 to obtain the user's detected glucose level.

Referring yet again to FIG. 1, the data processing terminal 105 may include a personal computer, a portable computer such as a laptop or a handheld device (e.g., personal digital assistants (PDAs)), and the like, each of which is configured for data communication with the receiver via a wired or a wireless connection. Additionally, the data processing terminal 105 may further be connected to a data network (not shown) for storing, retrieving and updating data corresponding to the detected glucose level of the user.

Figure 2:
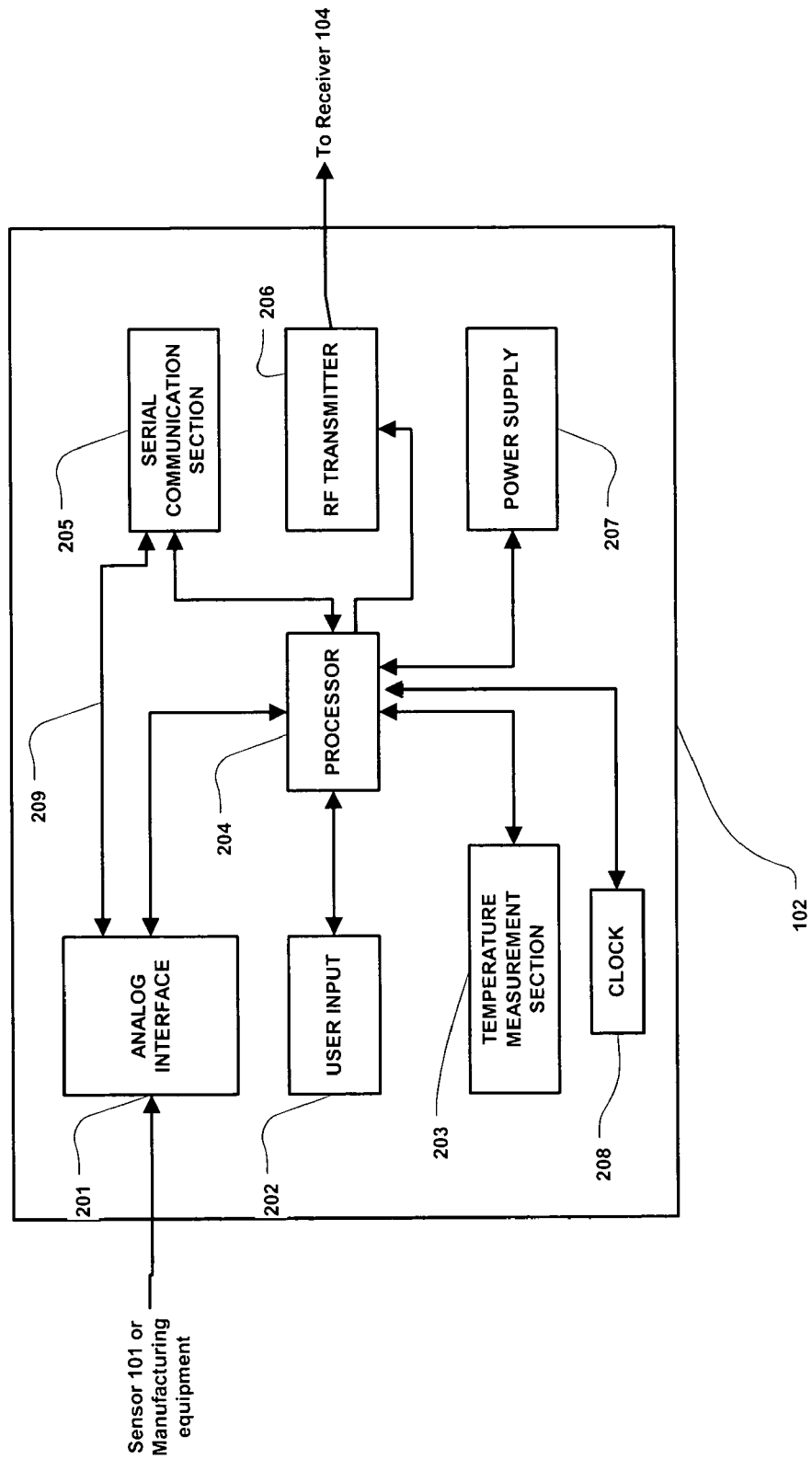
FIG. 2 is a block diagram of the transmitter of the continuous glucose monitoring system shown in FIG. 1 in accordance with one embodiment of the present invention.

FIG. 2 is a block diagram of the transmitter 102 of the continuous glucose monitoring system 100 in accordance with one embodiment of the present invention. The transmitter 102 includes an analog interface 201 configured to communicate with the sensor 101 (FIG. 1), a user input 202, and a temperature detection section 203, each of which is operatively coupled to a transmitter processor 204 such as a central processing unit (CPU). Further shown in FIG. 2 are a transmitter serial communication section 205 and an RF transmitter 206, each of which is also operatively coupled to the transmitter processor 204. Moreover, a power supply 207 is also provided in the transmitter 102 to provide the necessary power for the transmitter 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201, while a unidirectional output is established from the output of the RF transmitter 206. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, through the data path described above, the transmitter 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter 102 for operation upon completion of the manufacturing process as well as for direct communication for diagnostic and testing purposes.

Referring back to FIG. 2, the user input 202 includes a disable device that allows the operation of the transmitter 102 to be temporarily disabled, such as, by the user wearing the transmitter 102. In an alternate embodiment, the disable device of the user input 202 may be configured to initiate the power-up procedure of the transmitter 102.

As discussed above, the transmitter processor 204 is configured to transmit control signals to the various sections of the transmitter 102 during the operation of the transmitter 102. In one embodiment, the transmitter processor 204 also includes a memory (not shown) for storing data such as the identification information for the transmitter 102, as well as the data signals received from the sensor 101. The stored information may be retrieved and processed for transmission to the receiver 104 under the control of the transmitter processor 204. Furthermore, the power supply 207 may include a commercially available battery pack.

The physical configuration of the transmitter 102 is designed to be substantially water resistant, so that it may be immersed in non-saline water for a brief period of time without degradation in performance. Furthermore, in one embodiment, the transmitter 102 is designed so that it is substantially compact and light-weight, not weighing more that a predetermined weight such as, for example, approximately 18 grams. Furthermore, the dimensions of the transmitter 102 in one embodiment includes 52 mm in length, 30 mm in width and 12 mm in thickness. Such small size and weight enable the user to easily carry the transmitter 102.

The transmitter 102 is also configured such that the power supply section 207 is capable of providing power to the transmitter for a minimum of three months of continuous operation after having been stored for 18 months in a low-power (non-operating) mode. In one embodiment, this may be achieved by the transmitter processor 204 operating in low power modes in the non-operating state, for example, drawing no more than approximately 1 µA. Indeed, in one embodiment, the final step during the manufacturing process of the transmitter 102 places the transmitter 102 in the lower power, non-operating state (i.e., post-manufacture sleep mode). In this manner, the shelf life of the transmitter 102 may be significantly improved.

Referring again to FIG. 2, the analog interface 201 of the transmitter 102 in one embodiment includes a sensor interface (not shown) configured to physically couple to the various sensor electrodes (such as, for example, working electrode, reference electrode, counter electrode, (not shown)) of the sensor 101 (FIG. 1) of the monitoring system 100. The analog interface section 201 further includes a potentiostat circuit (not shown) which is configured to generate the Poise voltage determined from the current signals received from the sensor electrodes. In particular, the Poise voltage is determined by setting the voltage difference between the working electrode and the reference electrode (i.e., the offset voltage between the working electrode and the reference electrode of the sensor 102). Further, the potentiostat circuit also includes a transimpedance amplifier for converting the current signal on the working electrode into a corresponding voltage signal proportional to the current. The signal from the potentiostat circuit is then low pass filtered with a predetermined cut-off frequency to provide anti-aliasing, and thereafter, passed through a gain stage to provide sufficient gain to allow accurate signal resolution detected from the sensor 101 for analog-to-digital conversion and encoding for transmission to the receiver 104.

Referring yet again to FIG. 2, the temperature detection section 203 of the transmitter 102 is configured to monitor the temperature of the skin near the sensor insertion site. The temperature reading is used to adjust the glucose readings obtained from the analog interface 201. As discussed above, the input section 202 of the transmitter 102 includes the disable device which allows the user to temporarily disable the transmitter 102 such as for, example, to comply with the FAA regulations when aboard an aircraft. Moreover, in a further embodiment, the disable device may be further configured to interrupt the transmitter processor 204 of the transmitter 102 while in the low power, non-operating mode to initiate operation thereof.

The RF transmitter 206 of the transmitter 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Figure 3:
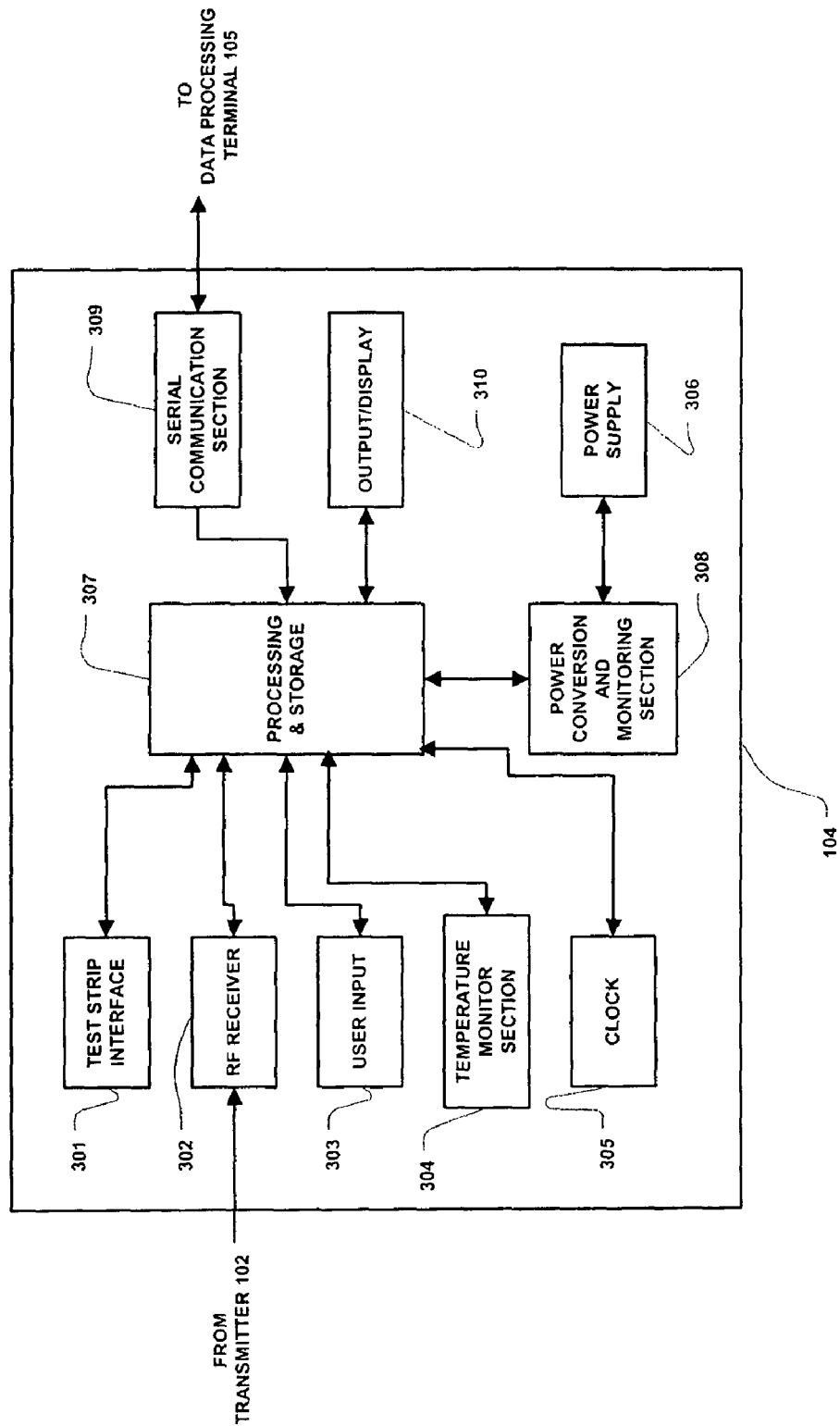
FIG. 3 is a block diagram of the receiver of the continuous glucose monitoring system shown in FIG. 1 in accordance with one embodiment of the present invention.

FIG. 3 is a block diagram of the receiver 104 of the continuous glucose monitoring system 100 in accordance with one embodiment of the present invention. Referring to FIG. 3, the receiver 104 includes a blood glucose test strip interface 301, an RF receiver 302, an input 303, a temperature detection section 304, and a clock 305, each of which is operatively coupled to a receiver processor 307. As can be further seen from the Figure, the receiver 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose testing strip, and thereby determine and display the glucose level of the testing strip on the output 310 of the receiver 104. This manual testing of glucose can be used to calibrate sensor 101. The RF receiver 302 is configured to communicate, via the communication link 103 (FIG. 1) with the RF transmitter 206 of the transmitter 102, to receive encoded data signals from the transmitter 102 for, among others, signal mixing, demodulation, and other data processing. The input 303 of the receiver 104 is configured to allow the user to enter information into the receiver 104 as needed. In one aspect, the input 303 may include one or more keys of a keypad, a touch-sensitive screen, or a voice-activated input command unit. The temperature detection section 304 is configured to provide temperature information of the receiver 104 to the receiver processor 307, while the clock 305 provides, among others, real time information to the receiver processor 307.

Each of the various components of the receiver 104 shown in FIG. 3 are powered by the power supply 306 which, in one embodiment, includes a battery. Furthermore, the power conversion and monitoring section 308 is configured to monitor the power usage by the various components in the receiver 104 for effective power management and to alert the user, for example, in the event of power usage which renders the receiver 104 in sub-optimal operating conditions. An example of such sub-optimal operating condition may include, for example, operating the vibration output mode (as discussed below) for a period of time thus substantially draining the power supply 306 while the processor 307 (thus, the receiver 104) is turned on. Moreover, the power conversion and monitoring section 308 may additionally be configured to include a reverse polarity protection circuit such as a field effect transistor (FET) configured as a battery activated switch.

The serial communication section 309 in the receiver 104 is configured to provide a bi-directional communication path from the testing and/or manufacturing equipment for, among others, initialization, testing, and configuration of the receiver 104. Serial communication section 309 can also be used to upload data to a computer, such as time-stamped blood glucose data. The communication link with an external device (not shown) can be made, for example, by cable, infrared (IR) or RF link. The output 310 of the receiver 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the receiver 104 also includes an electro-luminescent lamp configured to provide backlighting to the output 310 for output visual display in dark ambient surroundings.

Referring back to FIG. 3, the receiver 104 in one embodiment may also include a storage section such as a programmable, non-volatile memory device as part of the processor 307, or provided separately in the receiver 104, operatively coupled to the processor 307. The processor 307 is further configured to perform Manchester decoding as well as error detection and correction upon the encoded data signals received from the transmitter 102 via the communication link 103.

In conjunction with FIGS. 4, 5A, 5B, and 5C, a description is provided of a data packet from the transmitter 102 to the receiver 104 via the communication link 103.

FIG. 4 illustrates a data pack from the transmitter 102 (FIG. 1) in accordance with one embodiment of the present invention. Referring to FIG. 4, each data packet from the transmitter 102 includes 13 bytes as shown in the Figure. For example, the first byte (zero byte) includes the transmitter 102 identification information ("Tx ID"), while the third byte (byte two) provides transmitter status information, where a high nibble (byte) indicates an operating mode status, while a low nibble indicates a non-operating mode. In this manner, the signals received from the sensor 101 are packed into 13-byte data packs, for transmission to the receiver 104.

FIGS. 5A, 5B, and 5C illustrate a data packet table for Reed-Solomon encoding in the transmitter, a depadded data table, and a link prefix table, respectively, in accordance with one embodiment of the continuous glucose monitoring system of FIG. 1. Referring to FIG. 5A, it can be seen that the Reed Solomon encoded data block contents include 13 bytes of packed data (FIG. 4), one byte of the middle significant bit of the transmitter identification information (Tx ID), one byte of the most significant bit of the transmitter identification information, 232 bytes of zero pads, 8 bytes of parity symbols, to comprise a total of 255 bytes. In one embodiment, the Reed Solomon encode procedure at the transmitter 102 uses 8 bit symbols for a 255 symbol block to generate 8 parity symbols. Thereafter, the transmitter 102 is configured to remove the 232 bytes of zero pads, resulting in the 21 bytes of depadded data block including the 13 bytes of packed data as well as the 8 bytes of the parity symbols as shown in FIG. 5B.

Thereafter, a link prefix is added to the depadded data block to complete the data packet for transmission to the receiver 104. The link prefix allows the receiver 104 to synchronize with the transmitter 102 as described in further detail below. More specifically, as shown in FIG. 5C, the transmitter 102 is configured to add 4 bytes of link prefix (0x00, 0x00, 0x12, and 0x34) to the 21 bytes of depadded data block to result in 24 bytes of data packet. Once powered up and enabled in operational mode, the transmitter 102 is configured to transmit the 24 byte data packet once every minute. More specifically, the transmitter 102 is configured to Manchester encode the data at 2 bits per data bit (0=10; 1=01), and transmit the Manchester bits at 19,200 symbols per second. The transmitter 102 is configured to transmit the data packets with the most significant bit of byte zero first.

Figure 6:
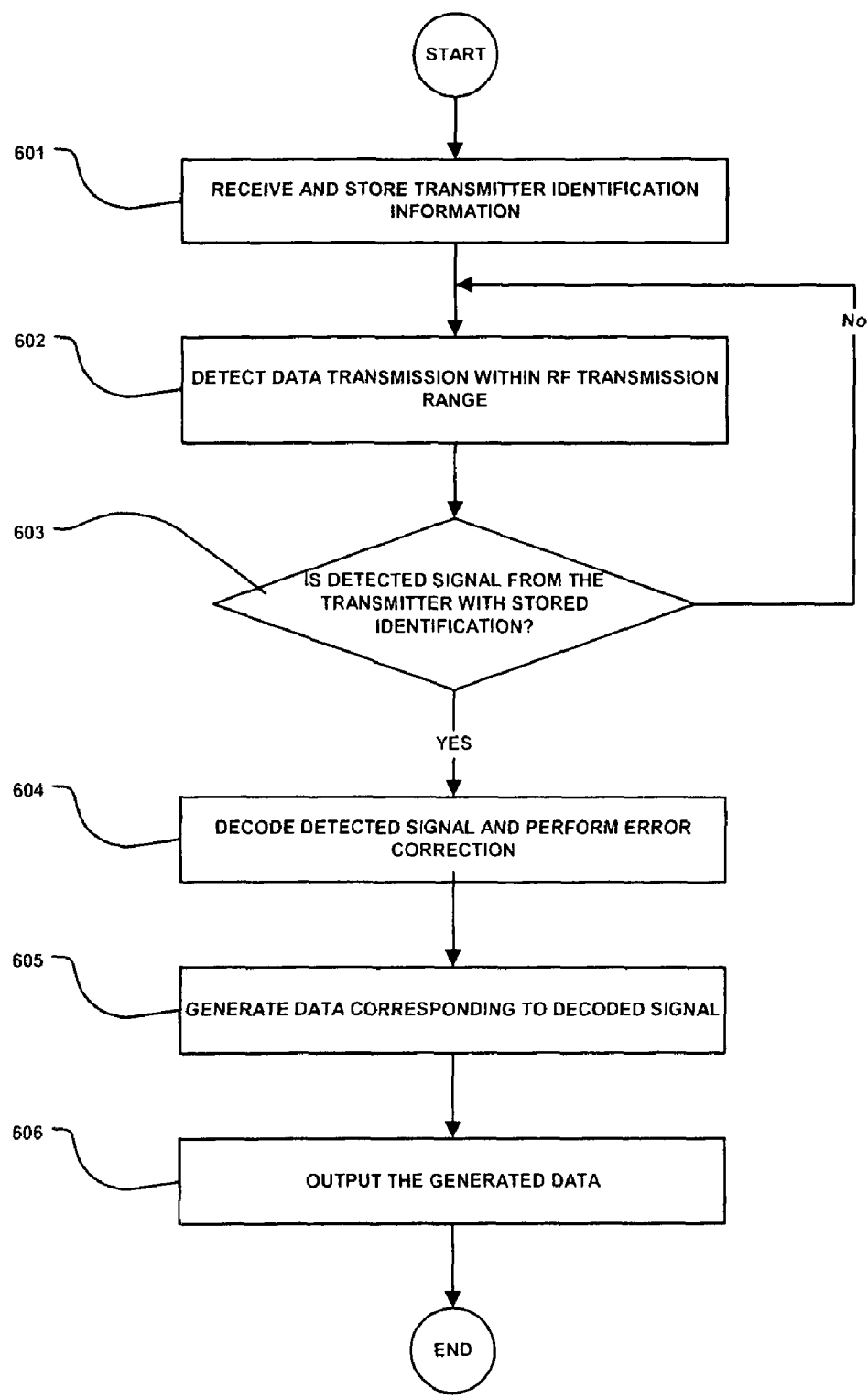
FIG. 6 is a flowchart illustrating the time hopping procedure for the receiver of the continuous glucose monitoring system shown in FIG. 1 in accordance with one embodiment of the present invention.

FIG. 6 is a flowchart illustrating the time hopping procedure for the receiver of the continuous glucose monitoring system shown in FIG. 1 in accordance with one embodiment of the present invention.

Referring to FIG. 6, upon completing the power up procedure as discussed above, the receiver 104 listens for the presence of a transmitter within the RF communication link range. At step 601, when the transmitter 102 is detected within the RF communication link range, the receiver 104 is configured to receive and store the identification information corresponding to the detected transmitter 102. Thereafter, at step 602, the receiver 104 is configured to detect (or sample) data transmission within its RF communication range. In one aspect, the receiver 104 is configured to identify a positive data transmission upon ascertaining that the data transmission is above a predetermined strength level for a given period of time (for example, receiving three separate data signals above the predetermined strength level from the transmitter 102 at one minute intervals over a period of five minutes).

At step 603, the receiver 104 is configured to determine whether the detected signals within the RF communication range is transmitted from the transmitter 102 having the transmitter identification information stored in the receiver 104. If it is determined at step 603 that the detected data transmission at step 602 does not originate from the transmitter with the stored transmitter identification information, then the procedure returns to step 602 and awaits for the detection of the next data transmission.

On the other hand, if at step 603 it is determined that the detected data transmission is from the transmitter 102 corresponding to the stored transmitter identification information, then at step 604, the receiver proceeds with decoding the received data and performing error correction thereon. In one embodiment, the receiver is configured to perform Reed-Solomon decoding, where the transmitted data received by the receiver is encoded with Reed-Solomon encoding. Furthermore, the receiver is configured to perform forward error correction to minimize data error due to, for example, external noise, transmission noise and so on.

Referring back to FIG. 6, after decoding and error correcting the received data, the receiver 104 at step 605 generates output data corresponding to the decoded error corrected data received from the transmitter 102, and thereafter, at step 606, the receiver 104 outputs the generated output data for the user as a real time display of the output data, or alternatively, in response to the user operation requesting the display of the output data. Additionally, before displaying the output data for the user, other pre-processing procedures may be performed on the output data to for example, smooth out the output signals. In one aspect, the generated output data may include a visual graphical output displayed on the graphical user interface of the receiver. Alternatively, the output data may be numerically displayed representing the corresponding glucose level.

Referring now to FIGS. 4 and 6, the time hopping procedure of one embodiment is described. More specifically, since more than one transmitter 102 may be within the receiving range of a particular receiver 104, and each transmitting data every minute on the same frequency, transmitter units 102 are configured to transmit data packets at different times to avoid co-location collisions (that is, where one or more receivers 104 cannot discern the data signals transmitted by their respective associated transmitter units 102 because they are transmitting at the same time.)

In one aspect, transmitter 102 is configured to transmit once every minute randomly in a window of time of plus or minus 5 seconds (i.e., it time hops.) To conserve power, receiver 104 does not listen for its associated transmitter 102 during the entire 10 second receive window, but only at the predetermined time it knows the data packet will be coming from the corresponding transmitter 102. In one embodiment, the 10 second window is divided into 400 different time segments of 25 milliseconds each. Before each RF transmission from the transmitter 102 takes place, both the transmitter 102 and the receiver 104 is configured to recognize in which one of the 400 time segments the data transmission will occur (or in which to start, if the transmission time exceeds 25 milliseconds.) Accordingly, receiver 104 only listens for a RF transmission in a single 25 millisecond time segment each minute, which varies from minute to minute within the 10 second time window.

Moreover, each transmitter 102 is configured to maintain a "master time" clock that the associated receiver unit 104 may reference to each minute (based on the time of transmission and known offset for that minute.). A counter also on the transmitter 102 may be configured to keep track of a value "Tx Time" that increments by 1 each minute, from 0 to 255 and then repeats. This Tx Time value is transmitted in the data packet each minute, shown as Byte 1 in FIG. 4. Using the Tx Time value and the transmitter's unique identification information (TX ID, shown as Byte 0 in FIG. 4), both the transmitter 102 and the receiver 104 can calculate which of the 400 time segments will be used for the subsequent transmission. In one embodiment, the function that is used to calculate the offset from the master clock 1-minute tick is a pseudo-random number generator that uses both the Tx Time and the TX ID as seed numbers. Accordingly, the transmission time varies pseudo-randomly within the 10 second window for 256 minutes, and then repeats the same time hopping sequence again for that particular transmitter 102.

In the manner described above, in accordance with one embodiment of the present invention, co-location collisions may be avoided with the above-described time hopping procedure. That is, in the event that two transmitters interfere with one another during a particular transmission, they are not likely to fall within the same time segment in the following minute. As previously described, three glucose date points are transmitted each minute (one current and two redundant/historical), so collisions or other interference must occur for 3 consecutive data transmissions for data to be lost. In one aspect, when a transmission is missed, the receiver 104 may be configured to successively widen its listening window until normal transmissions from the respective transmitter 102 resume. Under this approach, the transmitter listens for up to 70 seconds when first synchronizing with a transmitter 102 so it is assured of receiving a transmission from transmitter 102 under normal conditions.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A glucose monitoring system, comprising:
   a sensor configured to detect one or more glucose levels;
   a transmitter including a processor, the transmitter operatively coupled to the sensor to receive the detected one or more glucose levels, and to transmit signals corresponding to the detected glucose levels periodically; and
   a receiver operatively coupled to the transmitter to receive transmitted signals corresponding to the detected one or more glucose levels, and to synchronize with the transmitter;
   wherein the data communication between the transmitter and the receiver are synchronized based on a time variable or the transmitter is identified based on a data communication signal strength, and
   wherein the transmitter includes programming to transmit multiple data points within each of said signals that are transmitted periodically, the multiple data points including a current data point and at least one previous data point, such that where the receiver does not successfully receive the current data point from the transmitter, at a subsequent data transmission, the current data point is again transmitted to the receiver along with a new current data point, and the current data point is thereby received at the receiver and ascertained from the subsequent data transmission without retransmission of the multiple data points to the receiver or being lost.

2. The system of claim 1 wherein the receiver is operatively coupled to the transmitter via an RF communication link.

3. The system of claim 1 wherein the transmitter encodes the detected one or more glucose levels received from the sensor to generate encoded signals, the transmitter further transmitting the encoded signals to the receiver.

4. The system of claim 3 wherein the receiver decodes the encoded signals received from the transmitter.

5. The system of claim 3 wherein the transmitter transmits the encoded signals to the receiver at a transmission rate of once per minute.

6. The system of claim 1 wherein the transmitter transmits three data points per minute to the receiver, said three data points corresponding to the detected one or more glucose levels.

7. The system of claim 6 wherein said three data points include a current data point and two previous data points.

8. The system of claim 7 wherein the current data point corresponds to a current glucose level, and wherein the two previous data points include two consecutive glucose levels, said one of the two consecutive glucose levels immediately preceding the current glucose level.

9. The system of claim 1 wherein the receiver includes an output unit for outputting the received transmitted signals corresponding to one or more glucose levels.

10. The system of claim 9 wherein the output unit includes a display unit for displaying data corresponding to said one or more glucose levels.

11. The system of claim 10 wherein the display unit includes one of a LCD display, a cathode ray tube display, or a plasma display.

12. The system of claim 10 wherein the displayed data includes one or more of an alphanumeric representation corresponding to the one or more glucose levels, a graphical representation of the one or more glucose levels, or a three-dimensional representation of the one or more glucose levels.

13. The system of claim 10 wherein the display unit displays the data corresponding to the one or more glucose levels in real time.

14. The system of claim 9 wherein the output unit includes a speaker for outputting an audio signal corresponding to said one or more glucose levels.

15. The system of claim 1 wherein the receiver stores an identification information corresponding to the transmitter.

16. The system of claim 1 wherein the transmitter is encased in a water tight housing.

17. The system of claim 1 wherein the transmitter includes a disable switch for temporarily disabling the transmission of the signals.

18. The system of claim 1 wherein the transmitter is encased in a water tight housing.

19. The system of claim 1 wherein the transmitter includes a disable switch for temporarily disabling the transmission of the signals.

20. A glucose monitoring system, comprising:
a sensor configured to detect one or more glucose levels;
a transmitter operatively coupled to the sensor to receive the detected one or more glucose levels, and to transmit signals corresponding to the detected one or more glucose levels periodically; and
a receiver operatively coupled to the transmitter to receive transmitted signals corresponding to the detected one or more glucose levels and to synchronize with the transmitter based on a time variable or to identify the transmitter based on a signal strength;
wherein the transmitter transmits a current data point and at least one previous data point simultaneously in a single data transmission of the signals that are transmitted periodically, said current data point and said at least one previous data point corresponding to detected glucose levels, such that where the receiver does not successfully receive the current data point from the transmitter, at a subsequent data transmission, the current data point is again transmitted to the receiver along with a new current data point, and is thereby received at the receiver and ascertained from the subsequent data transmission without retransmission of the single data transmission to the receiver or being lost.

21. The system of claim 20 wherein the receiver is operatively coupled to the transmitter via an RF communication link.

22. The system of claim 20 wherein the transmitter encodes the detected one or more glucose levels received from the sensor to generate encoded signals, the transmitter further transmitting the encoded signals to the receiver.

23. The system of claim 22 wherein the receiver decodes the encoded signals received from the transmitter.

24. The system of claim 22 wherein the transmitter transmits the encoded signals to the receiver at a transmission rate of once per minute.

25. The system of claim 20 wherein the current data point corresponds to a current glucose level, and wherein said at least one previous data point includes at least two previous data points corresponding respectively to at least two consecutive glucose levels, said one of the at least two consecutive glucose levels immediately preceding the current glucose level.

26. The system of claim 20 wherein the receiver includes an output unit for outputting the received transmitted signals corresponding to one or more glucose levels.

27. The system of claim 26 wherein the output unit includes a display unit for displaying data corresponding to said one or more glucose levels.

28. The system of claim 27 wherein the display unit includes one of a LCD display, a cathode ray tube display, or a plasma display.

29. The system of claim 27 wherein the displayed data includes one or more of an alphanumeric representation corresponding to the one or more glucose levels, a graphical representation of the one or more glucose levels, and a three-dimensional representation of the one or more glucose levels.

30. The system of claim 27 wherein the display unit displays the data corresponding to the one or more glucose levels in real time.

31. The system of claim 26 wherein the output unit includes a speaker for outputting an audio signal corresponding to said one or more glucose levels.

32. The system of claim 20 wherein the receiver is configured to store an identification information corresponding to the transmitter.

33. A method of providing data communication in a glucose monitoring system, comprising:
detecting data transmissions within a predetermined RF transmission range periodically;
determining whether the detected data is transmitted from a transmitter;
synchronizing with the transmitter based on a time variable or identifying the transmitter based on a signal strength;
decoding the detected data, the detected data including a current data point and at least one previous data point in each detected data transmission of the periodic data transmissions, such that where the receiver does not successfully receive the current data point from the transmitter, then at a subsequent data transmission, the current data point is again transmitted to the receiver along with a new current data point, and is thereby received at the receiver and ascertained from the subsequent data transmission without retransmission of the detected data to the receiver or being lost; and
generating an output signal corresponding to the decoded data.

34. The method of claim 33 wherein the determining whether the detected data transmission is transmitted from the transmitter is based on an identification information received from the transmitter.

35. The method of claim 33 wherein the decoding further includes performing error correction on the decoded data.

36. The method of claim 33 wherein the decoding includes performing Reed-Solomon decoding on the detected data.

37. A glucose monitoring system, comprising:
a sensor configured to detect one or more glucose levels;
a processor operatively coupled to the sensor and a transmitter, the processor configured to process the detected one or more glucose levels to generate corresponding one or more signals for periodic transmission; and
a receiver operatively coupled to the processor configured to receive transmitted signals corresponding to the detected one or more glucose levels, the receiver configured to synchronize with the processor based on a time variable or to identify the transmitter based on a signal strength;
wherein the processor is configured to transmit a current data point and at least one previous data point simultaneously in a single data transmission of the signals that are transmitted periodically, said current data point and said at least one previous data point corresponding to detected glucose levels, such that where the receiver does not successfully receive the current data point, at a subsequent data transmission, the current data point is re-transmitted to the receiver with a new current data point, and is received at the receiver with the subsequent data transmission.

38. The system of claim 37 wherein the receiver is operatively coupled to the processor via an RF communication link.

39. The system of claim 37 wherein the processor is configured to execute a function to encode the detected one or more glucose levels received from the sensor to generate the encoded signals for periodic transmission.

40. The system of claim 39 wherein the receiver is configured to decode the received encoded signals.

41. The system of claim 39 wherein the periodic transmission includes a transmission rate of approximately once per minute.

42. The system of claim 37 wherein the current data point corresponds to a current glucose level, and wherein said at least one previous data point includes at least two previous data points corresponding respectively to at least two consecutive glucose levels, said one of the at least two consecutive glucose levels immediately preceding the current glucose level.

43. The system of claim 37 wherein the receiver includes an output unit for outputting the one or more of the periodically received signals corresponding to one or more glucose levels.

44. The system of claim 43 wherein the output unit includes a display unit for displaying data corresponding to said one or more glucose levels.

45. The system of claim 44 wherein the display unit includes one of a LCD display, a cathode ray tube display, or a plasma display.

46. The system of claim 44 wherein the displayed data includes one or more of an alphanumeric representation corresponding to the one or more glucose levels, a graphical representation of the one or more glucose levels, or a three-dimensional representation of the one or more glucose levels.

47. The system of claim 44 wherein the display unit is configured to display the data corresponding to the one or more glucose levels in real time.

48. The system of claim 43 wherein the output unit includes a speaker for outputting an audio signal corresponding to said one or more glucose levels.

49. The system of claim 37 wherein the receiver is configured to store an identification information corresponding to the transmitter.

* * * * *